United States Patent
Calio

(10) Patent No.: US 8,188,874 B2
(45) Date of Patent: May 29, 2012

(54) AIR SAMPLING SYSTEM HAVING INLINE FLOW CONTROL SWITCH

(75) Inventor: Rosario S. Calio, Exton, PA (US)

(73) Assignee: Veltek Associates, Inc., Malvern, PA (US)

( * ) Notice: Subject to any disclaimer, the term of this patent is extended or adjusted under 35 U.S.C. 154(b) by 425 days.

(21) Appl. No.: 12/402,738

(22) Filed: Mar. 12, 2009

(65) Prior Publication Data

US 2010/0171625 A1    Jul. 8, 2010

Related U.S. Application Data

(63) Continuation-in-part of application No. 12/068,483, filed on Feb. 7, 2008.

(51) Int. Cl.
*G08B 21/00* (2006.01)
(52) U.S. Cl. ............... 340/606; 454/187; 73/863.03
(58) Field of Classification Search .......... 340/603, 340/606, 609; 73/863, 863.01–863.03; 454/187; 700/215–217
See application file for complete search history.

(56) References Cited

U.S. PATENT DOCUMENTS

| | | | |
|---|---|---|---|
| 4,091,674 A | 5/1978 | Amey | |
| 4,604,111 A | 8/1986 | Natale | |
| 4,663,293 A | 5/1987 | Hempel et al. | |
| 4,813,984 A | 3/1989 | Griffis | |
| 5,421,214 A | 6/1995 | Burgdorfer | |
| 5,645,480 A | 7/1997 | Spengler | |
| 5,831,182 A | 11/1998 | Swenson | |
| 5,838,008 A | 11/1998 | Esler et al. | |
| 6,167,107 A | 12/2000 | Bates | |
| 6,216,548 B1 | 4/2001 | Park et al. | |
| 6,230,080 B1 * | 5/2001 | Lee et al. | 700/275 |
| 6,295,864 B1 | 10/2001 | You et al. | |
| 6,425,297 B1 | 7/2002 | Sharp | |
| 6,514,721 B2 | 2/2003 | Spurrell et al. | |
| 6,532,835 B1 | 3/2003 | Saaski et al. | |
| 6,692,953 B1 | 2/2004 | Sugita et al. | |
| 6,867,682 B2 | 3/2005 | Reinhardt et al. | |
| 7,667,839 B2 | 2/2010 | Bates | |

OTHER PUBLICATIONS

Veltek Associates, Inc., One Touch Command™ SMA™ Microbial Air Sampling Systems Brochure, Revised Dec. 2002, 4 pgs., Malvern, Pennsylvania.

* cited by examiner

*Primary Examiner* — Jeffery Hofsass

(57) ABSTRACT

A sampling system for quantifying the amount of contaminants in a controlled environment within a facility. The system has an air sampling devices each associated with a respective flow switch module, both within the controlled environment, and a first and second controller located outside the controlled environment. The first controller is in flow communication with the air sampling devices. The first controller is also in flow communication with the flow switch modules and controls a vacuum source to draw a predetermined volume of air through the at least one air sampling device via the at least one flow switch module at a desired flow rate. The flow switch module detects when the actual flow rate falls below or above a predetermined value, and generates an alarm.

41 Claims, 16 Drawing Sheets

AIR SAMPLING SYSTEM HAVING INLINE FLOW CONTROL SWITCH

RELATED APPLICATIONS

This application is a continuation-in-part of application Ser. No. 12/068,483, filed Feb. 7, 2008, for "System and Method for Air Sampling in Controlled Environments," which is hereby incorporated by reference.

BACKGROUND OF THE INVENTION

1. Field of the Invention

The present invention relates to devices and methods for collecting air samples in indoor environments. In particular, the present invention relates to devices and methods for collecting, processing and analyzing air samples in clean rooms, electrically and automatically controlling the sampling equipment, and calibrating the same.

2. Description of the Related Art

Clean rooms found in manufacturing, research, and other facilities are typically classified into two broad categories based on the static air pressure inside the rooms relative to atmospheric pressure and/or the air pressure in spaces adjacent the clean rooms. A positive air pressure room is maintained at an absolute air pressure greater than atmospheric pressure, greater than the air pressure in spaces adjacent the clean room, or both. The positive air pressure in such rooms is provided by pumping filtered and/or conditioned air into the rooms and controlling the flow of air out of the rooms. The adjacent spaces, which may be manufacturing facilities or offices, are typically maintained at or close to atmospheric pressure by heating, ventilation, and air conditioning (HVAC) systems, or by providing an opening to the environment that allows the adjacent spaces to equilibrate with atmospheric pressure. Thus, air flowing from the positive pressure clean room will flow toward the lower pressure in adjacent rooms or to the atmosphere.

When a positive air pressure clean room is breached, air flowing to adjacent spaces or the atmosphere is generally not a problem as long as airborne contaminants present in the clean room do not pose a potential adverse health effect. Typically, the air inside clean rooms in which electronics, aerospace hardware, optical systems, military equipment, and defense-related research are manufactured or conducted may not contain airborne gases, vapors, and particulate matter at concentrations that present a safety or health concern to human health or the environment. However, that is not always the case, as other operations within those industries may generate contaminants that are above acceptable levels and, therefore, must be prevented from escaping the clean room without treatment.

A negative air pressure room is maintained at an absolute air pressure that is either less than atmospheric pressure, less than the air pressure in spaces adjacent the clean room, or both. The negative pressure is maintained by pumping air out of the room. Negative pressure rooms are often used when there is a concern that contaminants in the air may pose a potential health threat to human health in adjacent spaces, or the environment.

Notwithstanding the human health and environmental implications, certain types of manufacturing and research operations must be conducted within a positive air pressure clean room to satisfy regulatory requirements and industry-adopted good manufacturing and laboratory quality control standards. For example, state and federal regulations, including those promulgated by the National Institute for Occupational Safety and Health (NIOSH), may necessitate the use of positive or negative pressure clean rooms.

In particular, the U.S. Food & Drug Administration (FDA) requires that pharmaceutical production be done within the confines of clean rooms that provide for the validation and certification that manufactured batches of pharmaceutical products are being done in a sanitary environment.

Positive and negative air pressure clean rooms have been used for many years. U.S. Pat. No. 4,604,111, for example, discloses a negative pressure apparatus and method for protecting the environment and populations from airborne asbestos and other particulate contamination inside a building, which includes an enclosure having a blower to pull air into a filtration unit inside the enclosure and dispel the filtered air to the atmosphere. U.S. Pat. No. 5,645,480 discloses the general features of a clean room.

Various FDA regulations and standards also specify requirements for air sampling and/or air monitoring equipment to be used inside clean rooms to verify or validate the cleanliness of the facility during certain drug manufacturing activities. The regulations also provide for electronic data recording, accuracy, precision, and record-keeping relating to monitoring the air quality within clean rooms. Similar requirements are imposed on other industries, such as the biotechnology industry.

U.S. Pat. No. 6,514,721 describes an air sampling device and method for collecting airborne pathogens and psychrometric data from a room or from remote air samples where the sample volume is electronically controlled by closely monitoring fan speed. The patent illustrates a device that draws room air into the device using a pump, which causes pathogen-containing particulates in the air to impact a growth/inhibitor media (a solid, liquid, gel, or mixture thereof) stored in a dish that is positioned within the sampling device. The patent states that previous sampling devices could not achieve a constant volumetric air flow of better than ±30% relative to a nominal or set-point flow rate, which caused a large variability in calculated concentrations of pathogens.

As the U.S. Pat. No. 6,514,721 patent suggests, one of the keys to successfully monitoring the air quality within a clean room is to ensure that the air flow rate through the air sampling/monitoring devices is very accurately determined during the time when a volume of air is collected. That fact is also appreciated in U.S. Pat. No. 4,091,674, which discloses an electronically timed, positive displacement air sampling pump for use with a wide variety of air sample collecting devices and in a wide range of environmental conditions. The disclosed invention is said to provide for accurate average flow rate, independently metered total volume, operating time register, and audible "rate fault" alarm. In that patent, accuracy is achieved by using a timing circuit coupled with mechanical bellows.

U.S. Pat. No. 6,216,548 illustrates a control system flow chart for an air sampling device for use in a controlled environment. In particular, the patent discloses a controller logic that involves turning on a pump, checking pressure, monitoring sampling time, drawing air into the sampler, shutting off the pump, and checking for leaks in the lines. The patent also teaches using a purge system for purging the lines and associated air particulate sampler using a purge gas such as nitrogen gas.

None of the prior art devices and air sampling methods described above are suitable for monitoring the level of contaminants in the air of a modern clean room, where issues of sample volume accuracy and precision, system control and monitoring, reporting, modularity, and remote monitoring are important. Accordingly, there exists a need for such a device and method for air sampling.

In addition, none of the prior art devices and air sampling methods described above have an inline flow switch to monitor the air flow realized at the air sampling device. Accordingly, there is a need for an air sampling system having an inline flow switch to monitor the air flow realized at the air sampling device, and to alert the user if the pressure supplied to the air sampling device is not within the desired tolerances.

SUMMARY AND OBJECTS OF THE INVENTION

The air sampling/monitoring system of the present invention is useful in clean rooms such as those operated by pharmaceutical, biotechnology, semi-conductor, and electronics industries, among others. The system is designed to test the air within a clean room to identify the level of viable contamination that is present in a volume of air. The system provides a controller and vacuum pump that are outside the clean room or aseptic areas of the facility, and provides a remote control touchpad and air sampling devices within the clean room/aseptic areas. The system requires hard wiring of both the vacuum tubing and electronic plenum wiring for the remote control touchpad. Highly accurate air flows through the system are achieved using a flow rate switch and programmable logic for setting the desired flow rate and acceptable deviations therefrom.

It is an object of the present invention to provide a method for collecting a volume of air from a controlled environment within a facility.

It is another object of the present invention to provide a method for controlling the flow rate of a fluid collected from a controlled environment within a facility.

It is still another object of the present invention to provide a sampling system for collecting a volume of air in a controlled environment within a facility, the volume of air being analyzed to quantify the presence of contaminants in the controlled environment.

It is another object of the present invention to provide a sampling system for quantifying the amount of contaminants in a controlled environment within a facility for achieving regulatory compliance.

It is still another object of the present invention to provide a system and method that takes advantage of wireless technology to reduce the number of structural penetrations between the controlled environment of a clean room and the space outside the clean room.

It is yet another object of the present invention to provide an air sampling system having an inline flow switch to monitor the flow at an air sampling device.

Briefly described, those and other objects and features of the present invention are accomplished, as embodied and fully described herein, by a system for collecting a volume of air in a controlled environment within a facility, which includes a controller located outside the controlled environment, the controller having a timer circuit, an flow rate circuit for providing a fluid flow, a flow switch, and a tube port in fluid communication with at least one air sampling device located within the controlled environment, wherein the flow rate circuit controls the flow switch and maintains the fluid flow at about a preprogrammed flow rate value; a vacuum pump in fluid communication with the air flow switch; and a touchpad wirelessly connected to the controller, wherein the touchpad includes a communications device for sending a start signal to the controller to collect the volume of air, and sending a stop signal to the controller when the volume of air has been collected.

Those and other objects and features of the present invention are accomplished, as embodied and fully described herein, by a method for collecting a volume of air from a controlled environment within a facility, including the steps of providing at least one air sampling device within the controlled environment; providing a first air sampling controller port outside the controlled environment in fluid communication with the at least one air sampling device; providing at least one touchpad controller within the controlled environment wirelessly connected to the first air sampling controller; providing a vacuum source in fluid communication with the first air sampling controller port; communicating a signal from the at least one touchpad to the vacuum source to draw a predetermined volume of air through the at least one air sampling device at an actual flow rate; and outputting a signal when the predetermine volume of air has been collected or when a flow rate through the at least one air sampling device falls below a programmed value. An inline flow switch is provided that monitors the air flow at the air sampling device, and alerts the user if the air flow is outside desired levels.

With those and other objects, advantages, and features of the invention that may become hereinafter apparent, the nature of the invention may be more clearly understood by reference to the following detailed description of the invention, the appended claims and to the several drawings attached herein.

BRIEF DESCRIPTION OF THE DRAWINGS

FIG. 13(*b*) is a diagram of the display used on the inline flow switch;

DETAILED DESCRIPTION OF THE PREFERRED EMBODIMENT

Figure 1:
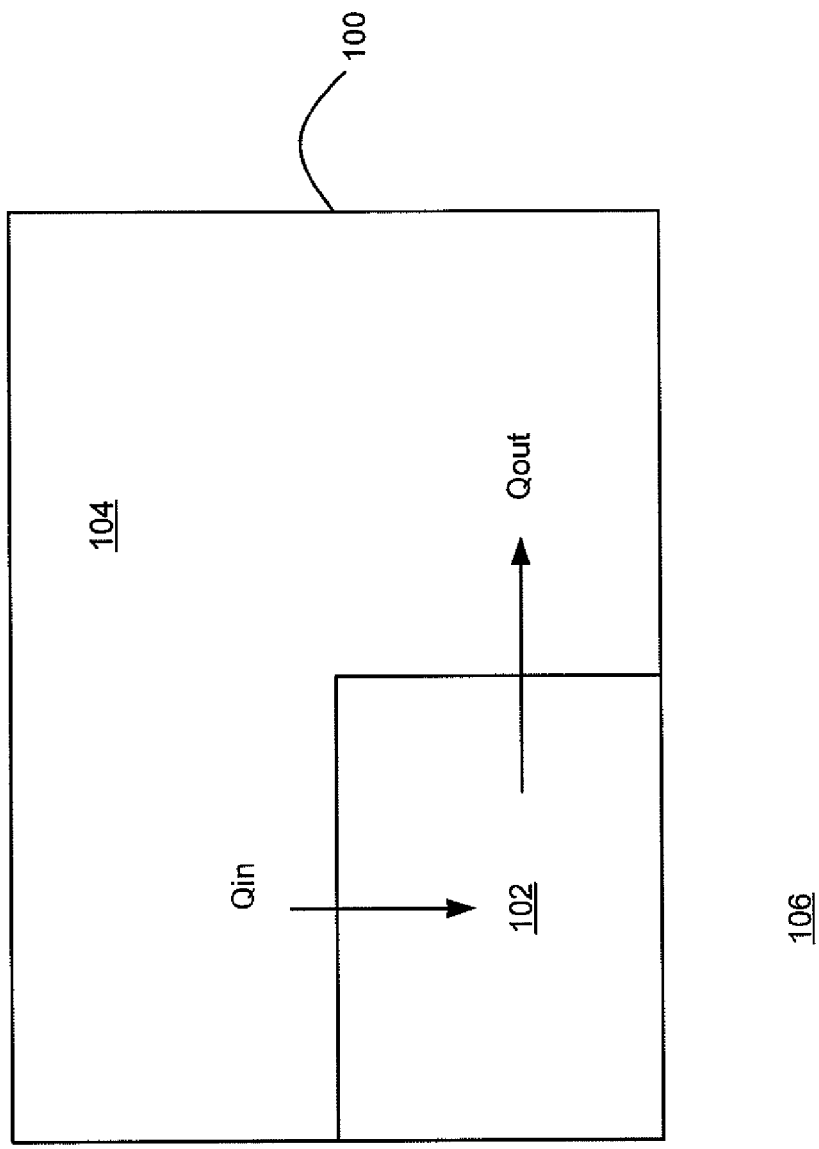
FIG. 1 is a schematic of an exemplary facility having a clean room therein according one aspect of the present invention.

Several preferred embodiments of the invention are described for illustrative purposes, it being understood that the invention may be embodied in other forms not specifically shown in the drawings.

Turning first to FIG. 1, shown therein is a schematic of an exemplary facility 100 having one or more clean rooms 102 therein. The clean room 102 is adjacent a space 104 and the outdoor atmosphere 106. The adjacent space 104 may be any one or more rooms within the same facility 100 that the clean room 102 is located and that adjoins the clean room 102, such as, for example, a separate manufacturing room, another clean room, a finish and fill room, a research laboratory, or offices. The clean room 102 and adjacent space 104 are separated by a divider, such as a wall.

The clean room 102 in the exemplary facility 100 is capable of being maintained at an air pressure $P_1$ that is less than the air pressure $P_2$ of the adjacent space 104, and also less than atmospheric air pressure $P_{ATM}$. This is accomplished by an HVAC system (not shown) that causes conditioned and filtered air to be pumped into the clean room 102 at a controlled flowrate $Q_{in}$ as depicted in FIG. 1. Air inside the clean room 102 that is pumped out of or otherwise flows out of the clean room 102 is represented by $Q_{out}$. As long as the difference between $Q_{in}$ and $Q_{out}$ is greater than zero, a positive pressure should be maintained in the clean room 102.

Figure 2:
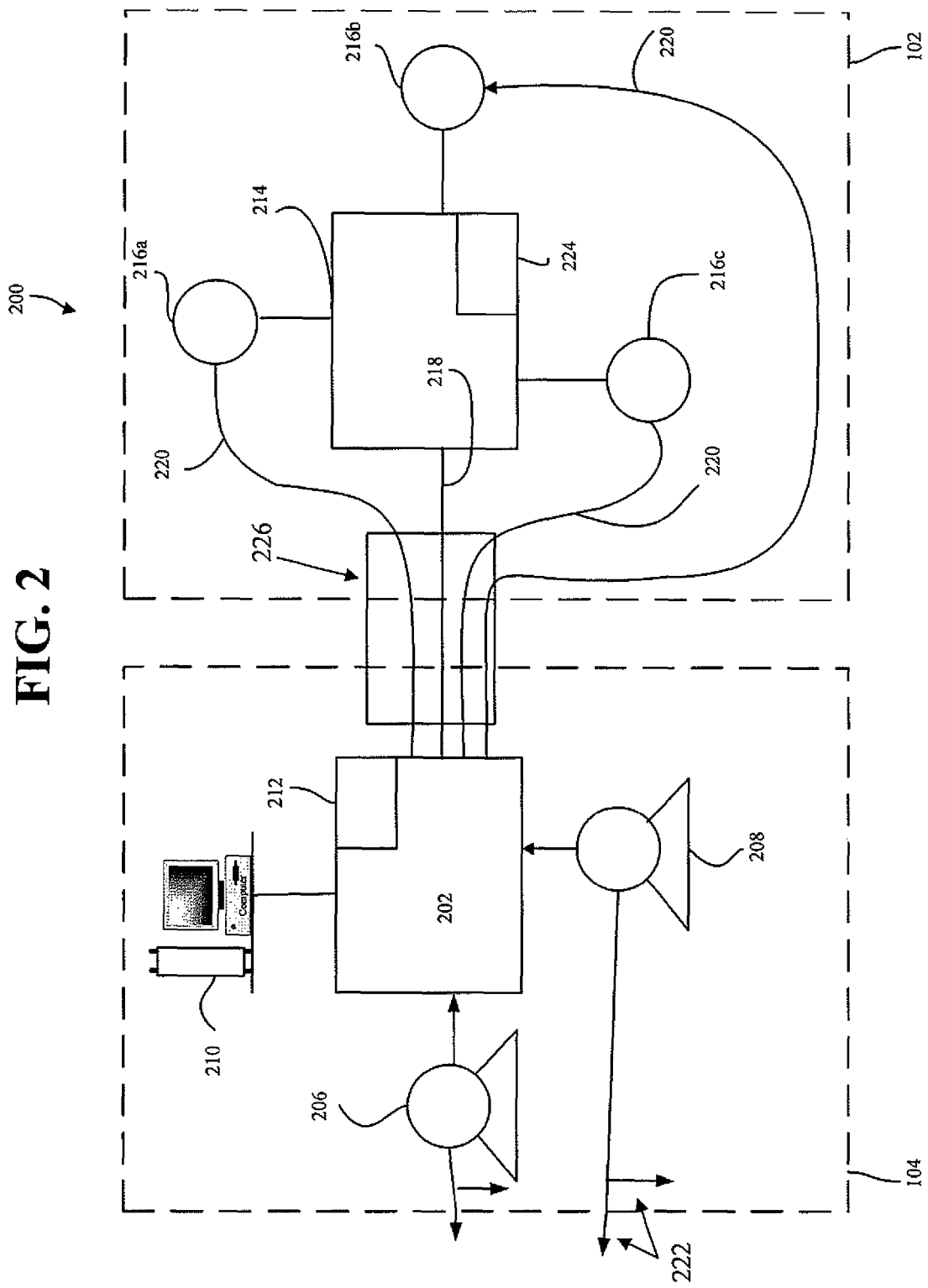
FIG. 2 is a block diagram of an air sampling/monitoring system according to one embodiment of the present invention for use in the clean room of FIG. 1.

Turning now to FIG. 2, shown therein is a block diagram of an air sampling/monitoring system 200 according to one embodiment of the present invention for use in sampling or monitoring the air in the clean room 102. The air sampling/monitoring system 200 includes a controller 202, a vacuum pump 208, an optional purge pump 206, and an optional computer 210, all of which may be co-located together in adjacent space 104 that is adjacent or remote from (i.e., not directly adjacent) the clean room 102.

Remotely connected to the controller 202 is a stand-alone wall-mountable or benchtop touchpad 214 and one or more air sampling devices 216a, 216b, 216c, . . . , 216n, where n is preferably 1-10, but that number is not limited by the air sampling/monitoring system 200 to any particular quantity of air sampling devices. That is, the system is linearly scalable above or below 10 air sampling devices. A typical air sampling device suitable for use with the present invention is the SMA™ Atrium by Veltek Associates, Inc., Malvern, Pa. The air sampling devices 216a, 216b, 216c, . . . , 216n according to the present invention may be any known air sampling device for collecting a volume of air. The terms "collecting," "sampling," "monitoring," and the like are not used to refer just to whole air sample devices, but also refer to devices that process a flow of fluid in order to separate certain gases, vapors, and particulate matter in the fluid for subsequent analysis and quantification. The terms "air" and "fluid" are used interchangeably to refer to gases, vapors, and particulates; thus, "air sampler" does not mean that only air is being collected.

Although FIG. 2 shows only a single touchpad 214 connected to multiple air sampling devices 216a, 216b, and 216c, it is also contemplated that there may be other arrangements of touchpads and air sampling devices. For example, there may be a one-to-one ratio of individual or discrete touchpads 214 and air sampling devices 216, or perhaps a single touchpad 214 may be connected to two or more air sampling devices 216a and 216b, while a separate touchpad 214 may be connected to a third air sampling device 216c.

The touchpad 214 is in communication with the controller 202 by wire 218, or using wireless means such as a receiver/transmitter 212 associated with the controller 202, and a receiver/transmitter 224 associated with the touchpad 214. The receiver/transmitters 212, 224 are on the same high frequency that is unique to the overall air sampling/monitoring system 200. The frequency is selected so as to reduce the likelihood of interference with other equipment in the facility 100, and to permit communications when the controller 202 and the touchpad 214 are remotely located from each other.

The one or more air sampling devices 216a, 216b, 216c are connected to a vacuum pump 208 (described below) by way of the controller 202 using one or more air tubes 220, which may be 0.25-inch vacuum tubing on the clean room 102 side of the air sampling/monitoring system 200, and ⅜-inch vacuum tubing on the adjacent space 104 side of the air sampling/monitoring system 200. Within the controller 202 is a manifold (not shown) that ties all of the individual air tubes 220 together and connects them to the vacuum side of the vacuum pump 208. Individual solenoids (not shown) associated with the air tubes 220 are used to turn on the air flow to each air sampling device 216.

The touchpad 214 and air sampling devices 216 are co-located together in the clean room 102, or in a portion of the clean room 102. The one or more air tubes 220 are connected to a wall-mounted quick disconnect outlet 226 located at the wall in the clean room 102.

The vacuum pump 208 is a demand pump that operates upon receiving a signal from the controller 202 to operate at the beginning of an air sampling cycle. It is powered by a standard alternating current provided by the facility 100 in which the air sampling/monitoring system 200 is installed, or by power from the controller 202 (or both). The vacuum pump 208 is connected to the controller 202 using 0.75-inch (inside diameter) vacuum tubing (other size tubing may also be used). The vacuum pump 208 according to one embodiment of the present invention is a 1.5 HP motor vacuum pump. The discharge from the vacuum pump 208 is directed outside the adjacent space 104, or within the adjacent space 104, as needed as shown by discharge tubes 222.

The optional purge pump 206 may be connected to the controller 202 using 0.25-inch (inside diameter) vacuum tubing (other size tubing may also be used). The discharge from the purge pump 206 is directed outside the adjacent space 104, or within the adjacent space 104, as needed. The discharge will most likely be processed through an abatement system (not shown) to collect or scrub purge gases and contaminants collected during the purge cycle (described below).

The computer 210 may be used as a data recorder. The computer 210 may be a dedicated computing device; however, if a dedicated or network computing device is already installed at the facility 100, the computer 210 is not needed for data recording purposes. Data recorded by the computer 210 include time of sample, sample date, length of sample, and sample location, among other data.

Figure 3:
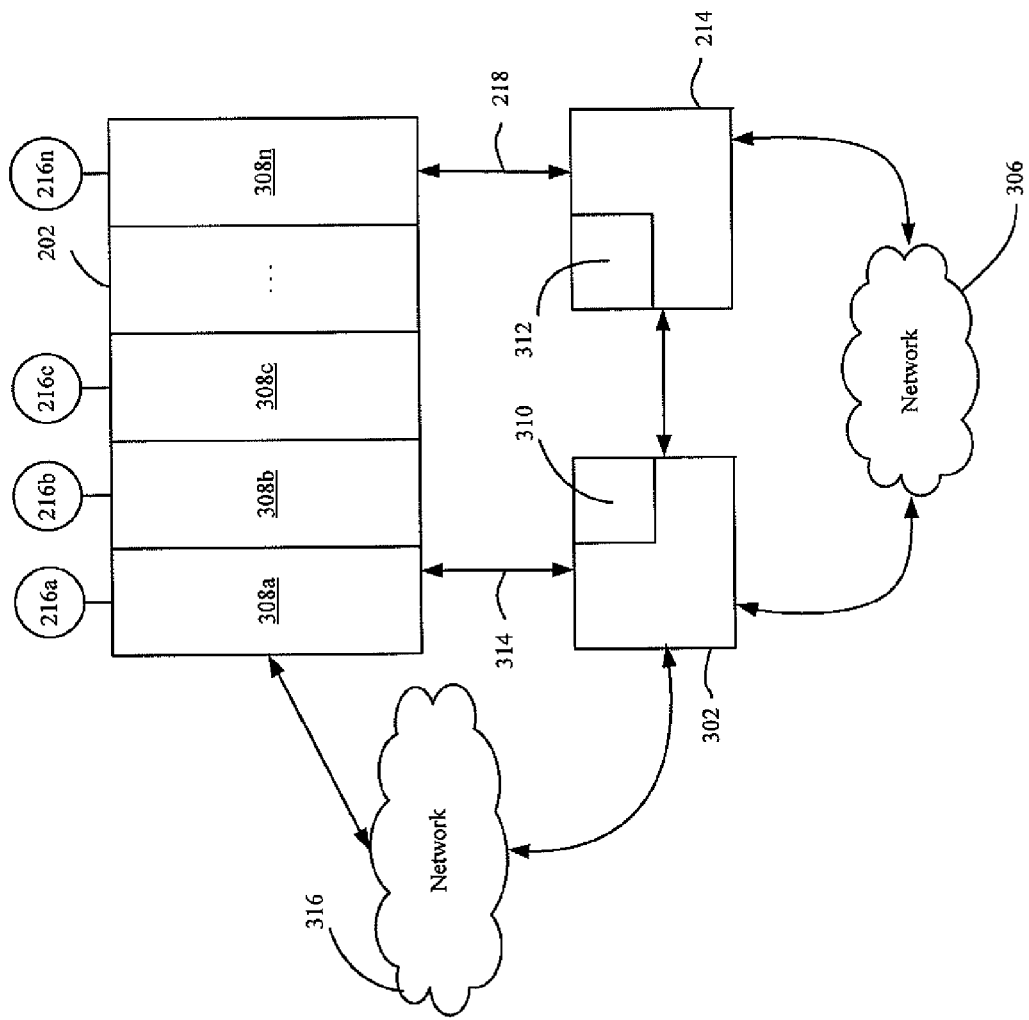
FIG. 3 is a block diagram of a controller connected to a base station and a touchpad according to one embodiment of the present invention.

Turning now to FIG. 3, shown therein is a block diagram of the controller 202 of the present invention connected to a base station 302 and a touchpad 214. The controller 202 includes one or more individual modular ports 308a, 308b, 308c, . . . , 308n, for connecting the controller 202 to the individual air sampling devices 216a, 216b, 216c, . . . , 216n, respectively, and one or more touchpads 214 (only one touchpad 214 is shown). The simplest configuration would be a single controller 202 having a single port 308a in one room, connected to one or more air sampling devices 216 and a single touchpad 214 in another room. An additional port 308b can then be added to the controller 202 to connect with an additional one or more air sampling devices 216 (and the touchpad 214 can be updated to have an interface that controls the second air sampling device 216 or a second touchpad 214 may be used). The touchpad 214 and air sampling devices 216 of the port 308b can be in the same room as the touchpad 214 and the air sampling devices 216 for the port 308a, but in a different area of that room, or can be in an entirely different room. The ports 308a, 308b, 308c, ..., 308n are further modular because they include their own dedicated power, hardware and software, including fittings and connectors necessary for operation. In other words, the modularity makes the system easily configurable by adding or removing ports 308a, 308b, 308c, ..., 308n to connect with individual touchpads 214 and their associates one or more air sampling devices 216a, 216b, 216c, ..., 216n, respectively.

Although FIG. 3 shows the touchpad 214 connected to a single port 308n, it can be connected to each of the ports 308a, 308b, 308c, ..., 308n and, indirectly to each of the air sampling devices 216a, 216b, 216c, ..., 216n, respectively (or directly connected to each of the air sampling devices, as best shown in FIG. 2). The controller 202 passes signals between the touchpad 214 and the sampling device 216 connected to a particular port 308. Thus, the control signals send from the touchpad 214 or the port 308a are sent to the air sampling device 216 also connected to that same port 308a, but not to the air sampling device 216 connected to the port 308b.

Because the controller 202 is modular, it may have any number of ports n, depending upon the needs of the clean room 102 (or clean rooms) as specified, for example, in the individual facility air sampling protocol, standard operating procedures, quality assurance/quality control plans, regulations, etc. For example, the controller 202 may be used to control 1, 2, 3, ... n air samplers deployed within one or more clean rooms 102, in which case it will have a corresponding number of ports. Preferably, one or more of the individual air sampling devices 216a, 216b, 216c, ..., 216n, and one touchpad 214 are connected to each one of the individual ports 308a, 308b, 308c, ..., 308n.

Each of the individual ports 308a, 308b, 308c, ..., 308n include at least a connector for connecting the individual ports 308a, 308b, 308c, ..., 308n to data loggers, such as the computer 210, or to other devices. Preferably, at least two multi-pin connectors are used. Pairs of multi-pin connectors are electrically connected in parallel. A suitable pin connector would include, but is not limited to, a 9-pin connector.

The base station 302 is needed in case the touchpad 214 is designed without wireless communications features for communicating with the controller 202. The base station 302 may be co-located with the controller 202, or otherwise outside the clean room 102, or it may be co-located with the touchpad 214 inside the clean room 102. The base station 302, which acts primarily as a data communications relay between the touchpad 214 and the controller 202, may be operatively connected to the touchpad 214 via a data communications network 306 such that the touchpad 214 does not need to be directly connected to the controller 202 (i.e., it may be connected wirelessly). The data communications network 306 may be any proprietary or public network, including a packet-switched network, such as the Internet, a local area network, a wireless network, or a combination of networks. Communications between the base station 302 and the touchpad 214 via the data communications network 306 could be facilitated by receiver/transmitters 310, 312.

The controller 202 and the base station 302 may be operatively connected to each other by cable 314, or via a wired or wireless data communications network 316 using an integrated radio with digital input/outputs (not shown). The data communications network 316 may be any proprietary or public network, including a packet-switched network, such as the Internet. The receiver/transmitters of the controller 202 and the base station 302 are on the same high frequency that is unique to the overall air sampling/monitoring system 200. The frequency is selected so as to reduce the likelihood of interference.

The base station 302 interface operates as a two-way (point to point) monitoring and control device with expandable input/output options. The receiver/transmitter 310 located in the base station 302, and the receiver/transmitter 312 located in the touchpad 214 located in the clean room 102 are a dedicated pair that only communicate with each other. The receiver/transmitters 310, 312 connect to input/output circuit boards that observe that the individual ports 308a, 308b, 308c, ..., 308n are powered up, are in an air sampling mode, and broadcast an air flow error during an air sampling cycle. The base station 302 can detect the state of activity of each of the individual ports 308a, 308b, 308c, ..., 308n. The base station 302 located near the controller 202 has an input/output that is cabled directly to its corresponding port 308a, 308b, 308c, ..., 308n in the controller 202.

Figure 4:
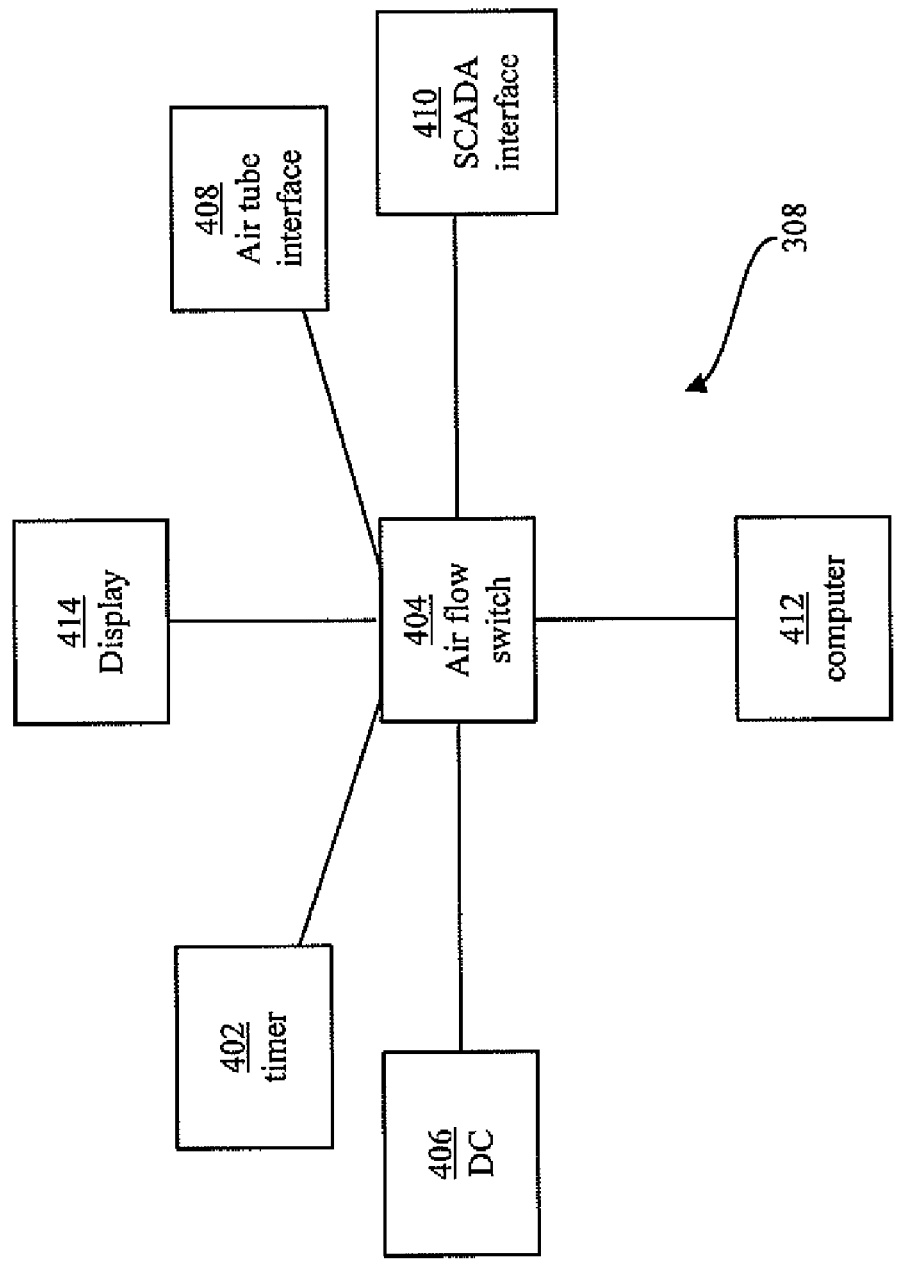
FIG. 4 is a block diagram of a port of the controller shown in FIG. 3.

Turning now to FIG. 4, shown therein is a block diagram of an exemplary port 308 of the controller 202 according to one embodiment of the present invention. The port 308 has its own dedicated timer 402, air flow switch 404, direct current power supply 406, air tube interface 408, facility System Control and Data Acquisition (SCADA) interface 410, and computer 412. The port 308 is modular and independent of other ports associated with the controller 202, as previously described. Thus, in the event the port 308 fails, the remaining ports associated with the controller 202 can continue to function within calibration tolerances. The modular design also removes the possibility of a single point system failure. The port 308 has its own direct current power 406, and is not dependent on a centralized power source to operate. Ground loop or direct current voltage shifts are eliminated by using optical coupling circuits (not shown), thus providing stable and robust performance. These circuits isolate the SCADA direct current ground and the SCADA voltage distribution system from the direct current voltage and ground distribution system (not shown) of the controller 202. If a facility system is present, it and the controller 202 will not depend on a common direct current ground bus connection. This enables the facility system and the controller 202 to be connected with long cables without extraordinary direct current ground interconnection between the two systems. The facility system sends a current signal or receives a current signal that is referenced to the facilities' direct current power system. This is a safe and effective way of eliminating the interconnection of two systems that have different power requirements.

The dedicated timer 402 is used to monitor the air sampling cycle duration. The timer 402 may be located at the controller 202 outside the clean room 102, or at the touchpad 214 inside the clean room 102 and connected to the controller 202 via line 218. The status of the timer 402 for the port 308 is observable at the controller 202 and/or at the touchpad 214. Each timer 402 may run independently or simultaneously with other ports 308. The timer 402 may be calibrated to a known standard to obtain very accurate readings. The timer 402 starts the air sampling cycle and issues commands through its input/output to open solenoids (not shown) and start the vacuum pump 208. The timer 402 lets the air flow switch 404 know that a sampling cycle has been initiated and declares a 1 cfm error signal if the proper air flow is not present. The timer 402 also provides +12 volts direct current power to other components of the port 308 and touchpad 214.

The controller 202 has an internal interface that can connect to a customer's SCADA interface 410, or computer 412, or a programmable logic controller (PLC) that can interface with a monitoring system associated with the facility 100. The controller 202 includes an isolator interface (not shown) that will not create any voltage shifts or ground loops when connected to a facility system, which can cause information problems for the facility or the controller 202. The purge mode of the controller 202 is not interfered with or affected by the wireless controls or isolation interface input/outputs of the system 200.

The nominal or set-point volumetric flow rate through each of the one or more air sampling devices 216a, 216b, 216c is 1 cfm (or 30 lpm). This is accomplished by the 1 cfm circuit and the air flow switch 404. The air flow switch 404 includes a digital air flow display 414 that may be programmed to display air flow rate in liters per minute (lpm), cubic feet per minute (cfm), or other units. The air flow switch 404 generates an error signal if the air flowing through the port 308 during an air sampling cycle, T, does not meet a pre-programmed or set-point 1 cfm air flow value or satisfy predetermined tolerances. The signal allows the user to be alerted to a problem with a particular air sample. Because the air flow switch 404 is a digital switch, it may be easily calibrated against a standard flow switch (such as a National Institute of Standards and Technology-certified switch), and it is insulated from affects caused by pressure variations in the air flow tubing or the location of the air flow switch 404. A digital flow switch also eliminates internal piping variations from system to system, and it has an integrated flow adjustment pinch valve, which reduces piping.

The air flow switch 404 is mechanically and electrically connected to an air tube interface 408, which receives air tube 220 to provide a physical connection between the air flow switch 404 of the port 308 and a remote air sampling device 216 (as shown in FIG. 2). While a digital air flow switch 404 is preferred, a float type meter (rotameter) could also be used, if pressure variations are taken into account. Rotameters are less desirable because, among other things, it may be necessary to provide a calibration conversion device and computed transfer function, and the rotameter must be positioned at a suitable level and angle to permit accurate manual readings.

The air flow switch 404 sits between the one or more air sampling devices 216a, 216b, 216c and the 1 cfm circuit, and is designed to maintain a steady-state flow rate through the one or more air sampling devices 216a, 216b, 216c and associated air tubing 220, with a detectable air flow rate deviation tolerance of ±3-percent from the nominal set-point flow rate (typically, the concern is when the flow rate decreases 3% from the nominal set-point flow rate). This air flow rate accuracy, which provides a margin of error of about 2-percent for a system calibrated for ±5-percent, for example, is achieved through a combination of routine and non-routine calibration checks using a standard flow switch, as discussed above, and software and hardware that constantly monitors flow rate in real-time or near real-time. The air flow switch 404 is programmed to send an error signal to a 1 cfm circuit board (not shown) when the air flow is below the programmed set-point or low-flow value. That is, the flow switch 404 informs the 1 cfm circuit that the air flow is below the 3-percent minimum level programmed into the system. The 1 cfm circuit checks to ensure the air flow rate error is valid. If the circuit confirms the validity of the air flow, it sends a signal to the individual port 308a, 308b, 308c, . . . , 308n that is doing the air sampling.

The flow switch 404 has low and high set-points, which are programmable. When the air flow is too far above or below the set-point values, the flow switch 404 sends a digital "on" signal to the 1 cfm circuit that the air flow is in error. The 1 cfm circuit is active during an air sampling cycle, and a signal from the flow switch 404 will cause the 1 cfm circuit to send or broadcast a flow error to the controller 202, touchpad 214, wireless control panels, and an isolator controller 504 (FIG. 5).

The SCADA interface 410 allows the port 308 to connect to a facility SCADA, which allows the air sampling/monitoring system 200 to be integrated into other facility data collection and monitoring systems. The isolation interface prevents the present system from compromising the controller or the SCADA system performance by eliminating ground loops and voltage shifts when connecting to third-party equipment, as previously described.

The port 308 may be directly connected to, or interconnected to, a separate computer 412 in addition to being connected to the touchpad 214. The separate computer 412 has software and hardware to implement the functions of the port 308. The separate computer 412 can be a processor with memory. The controller 202 may also have a central processor, and the separate computer 412 communicates with that processor to control the overall operation of the controller 202 and the air sampling/monitoring system 200.

Figure 5:
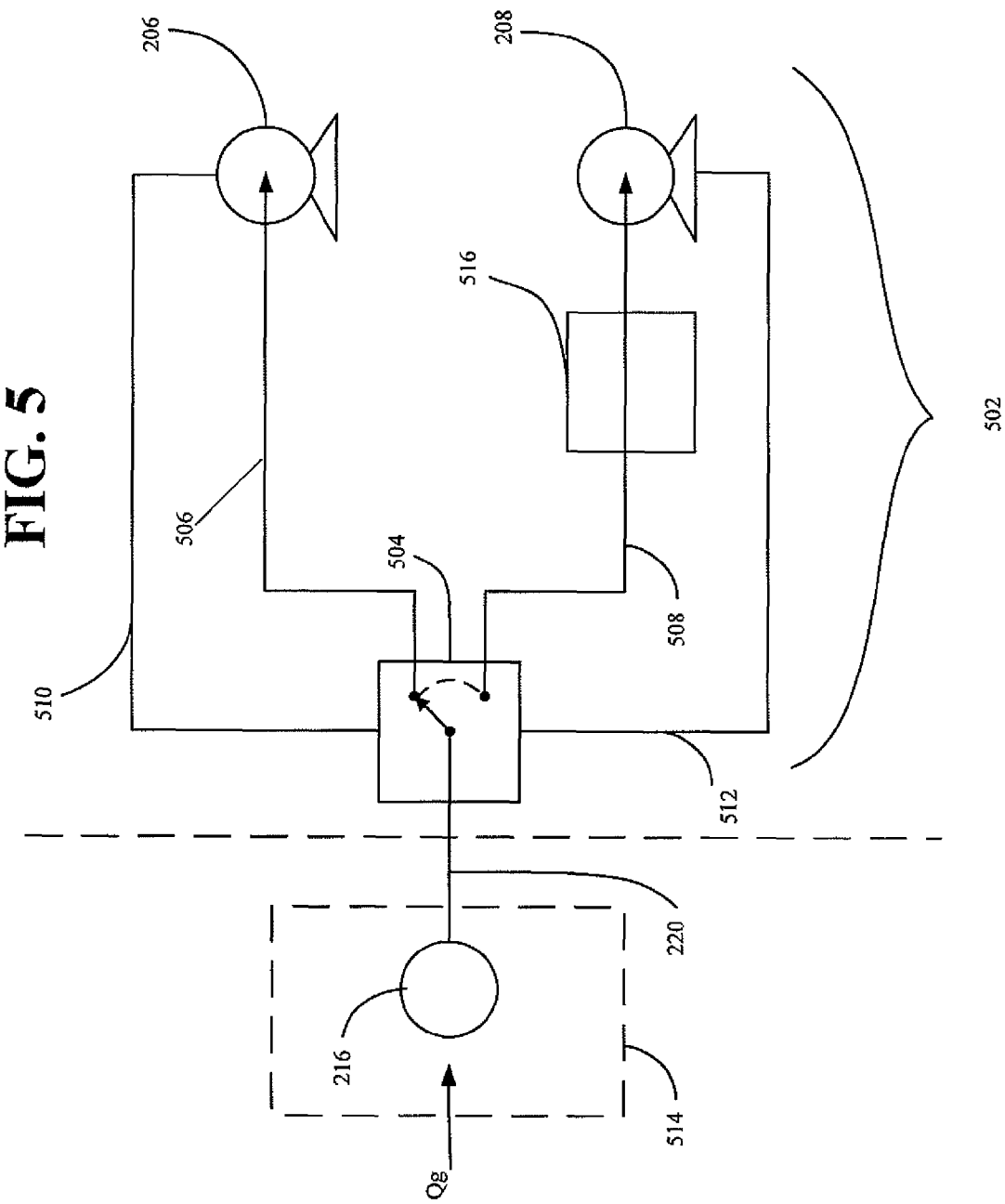
FIG. 5 is a block diagram of a purge system for purging the air sampling devices according to one embodiment of the present invention.

Turning now to FIG. 5, shown therein is a purge system 502 for purging the air sampling devices 216a, 216b, 216c, . . . , 216n and associated air tubes 220 to ensure there is no residual contaminants in those portions of the air sampling/monitoring system 200. An isolator controller 504 controls operation of the vacuum pump 208 and purge pump 206 in accordance with an air sampling cycle and a purge cycle. In the air sampling cycle, the isolator controller 504, which can be a three-way solenoid, causes the vacuum pump 208 to stop by sending a signal to the vacuum pump 208 via an electrical connection 512. At the same time, the isolator controller 504 controls the purge pump 206 to engage by sending a signal to the purge pump 206 via an electrical connection 510. When those signals are sent, air is not pulled through the air sampling devices 216a, 216b, 216c, . . . , 216n and air tube 508 by the vacuum pump 208, but is instead pulled through the air sampling devices 216a, 216b, 216c, . . . , 216n and air tube 506 by the purge pump 206. Thus, during the air sampling cycle, air flow is steered to the vacuum pump 208 and the purge path is closed. The opposite is done during the purge cycle, whereby air flow is steered to the purge pump 206 and the air sampling path is closed.

Although the isolator controller 504 preferably is associated with up to 10 individual ports 308 and corresponding air sampling devices 216, FIG. 5 shows only one port/air sampling device. During any air sampling cycle, the controller 202 is prevented from initiating a purge cycle. However, once the air sampling cycles for each of the air sampling devices 216 are complete, the controller 202 is set in the purge mode. The isolator controller 504 ports each have a dedicated solenoid (not shown) that will direct the air collected during the purge cycle to a purge exit 222 (as best seen in FIG. 2).

Figure 6:
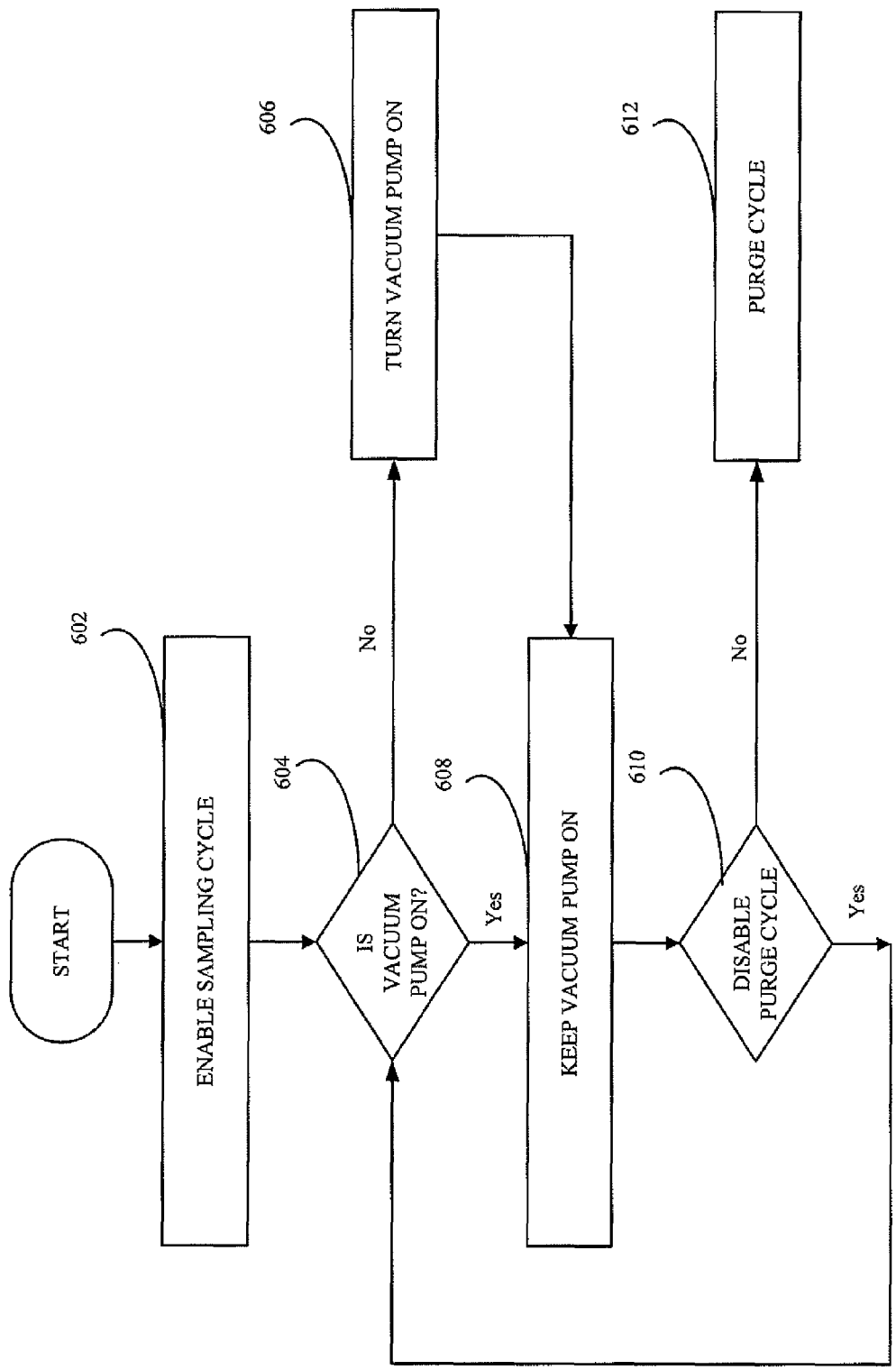
FIG. 6 is a process flow diagram illustrating an isolator controller logic.

FIG. 6 is a process flow diagram illustrating the isolator controller logic according to one embodiment of the present invention. In step 602, the process enables the air sampling cycle, which is the normal operation of the system. In step 604, the isolator controller 504 checks if the vacuum pump 208 is on. If the vacuum pump 208 is on, then the purge pump 206 is necessarily off, since the isolator controller 504 can only enable the vacuum pump 208 or the purge pump 206 at any one time. If the vacuum pump 208 is not on, then the vacuum pump 208 is turned on in step 606. This can be accomplished automatically based on a preprogrammed time or operation, or manually by entering a command at a remote computer 210 or at the local touchpad 214.

In step 608, the isolator controller 504 keeps the vacuum pump 208 on. In step 610, the isolator controller 504 checks to see if the purge cycle should continue to be disabled. If so, the process returns to step 604 and the sampling cycle continues. Once the isolator controller 504 receives a signal from the controller 202 to enter the purge cycle, in step 612, the isolator controller 504 starts the purge cycle. At the end of the purge cycle, the isolator controller 504 returns to the air sampling cycle, at step 604, or possibly shuts off the system until the next air sampling system starts. In general, the purge cycle will run until the next air sampling cycle is scheduled, which could be, for example, once every 24 hours. In some clean rooms 102, such as a class 100 clean room, it may not be necessary to run a purge cycle during the period when the air sampling cycle is not being performed. The isolator controller logic is implemented by an isolator printed circuit board (not shown) that interfaces with the SCADA (typically operated by a PC) or programmable logic controllers. The board eliminates the joining of the facility voltage system with the power system of the present invention.

The isolation circuit board is located in the controller 202 and can be connected to the SCADA or to a programmable logic controller system. All commands and observations can be made at the touchpad 214. The wireless and isolation features of the system 200 can be implemented on any of the three interfaces connected to the controller 202. For example, when a wireless panel receives a command to start an air sampling cycle, the touchpad 214, the controller 202, and the computer 210 will each observe the air sampling cycle in progress. Also for example, when a air flow error is detected, the controller 202 can broadcast the error detected in a particular port 308 to the touchpad 214 and the computer 210 (or any other input/output device connected to the system 200 that may be used).

The purging cycle involves injecting steam, hydrogen peroxide, or other vapor/gas into the air flow through the air sampling devices 216a, 216b, 216c, . . . , 216n and air tube 220. This may be accomplished by isolating the air sampling devices 216a, 216b, 216c, . . . , 216n in one or more isolator chambers 514 and introducing a flow of purging gases at flow rate $Q_g$ into the chamber when the purge cycle is turned on. The isolator chamber 514 does not have or allow any human contact inside the enclosure. Other techniques for purging and decontaminating air tubes are well known in the art. Users of the present system involved in pharmaceutical manufacturing operations will desire to sanitize various system components before any drug substances are mixed and before commencing with finish and fill operations. The purge mode of the present invention allows the sterilization of the tubes directly connected to the isolator. The purge vapor/gas exits the isolator controller 504. During the isolated purging cycle, the air flowing through the air tube 508 may be conditioned by gas conditioning device 516, which may comprise particulate filters (not shown), organic adsorbents, activated charcoal, a knockout drum, cyclone, or other substance or device, or combination of substances and devices.

Figure 7:
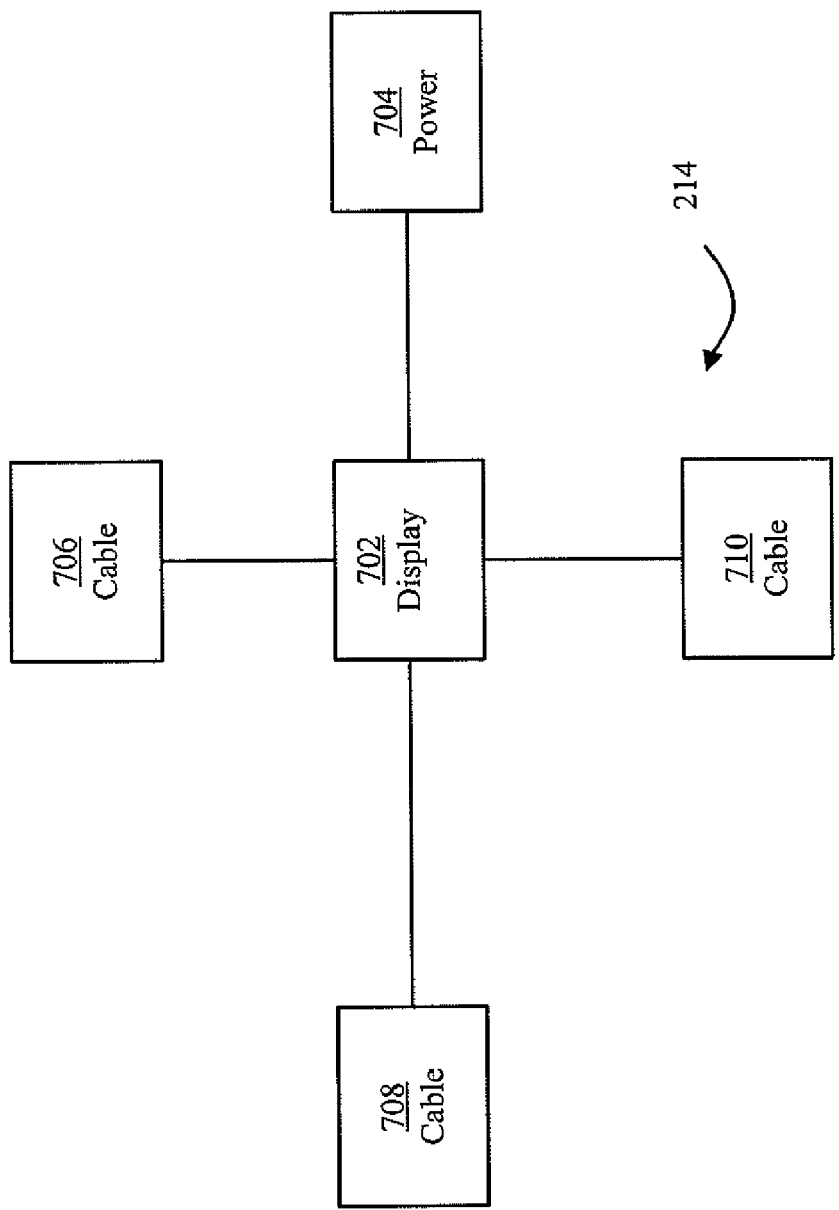
FIG. 7 is a block diagram of a touchpad according to one aspect of the present invention.

Turning now to FIG. 7, shown therein is a block diagram of a touchpad 214 according to one aspect of the present invention. The touchpad 214, as discussed previously, may be a static wall-mounted device, or it may be portable and adapted to being located on any flat surface, such as a bench, inside a working area of the clean room 102. The touchpad 214 is the human interface input/output device for the air sampling/monitoring system 200. It remotely controls the controller 202 which is located outside the clean room 102. This design removes most of the electronics of the system from the aseptic areas of the clean room 102, including the system power supply, flow switch circuitry, and other electronics. The touchpad 214 electronics are sealed inside the device so that the device may be disinfected like other portions of the clean room 102.

The touchpad 214 allows the user to start, stop, program, and monitor the air sampling and purge cycles within the clean room 102. It also allows the user to abort an air sampling cycle, hear an audible signal or observe a visible signal when an air sampling cycle is complete, observe an airflow error if one is detected during an air sampling cycle, and activate an alarm. For example, a visible signal may be generated when the system detects a 1 cfm air flow error above or below a pre-programmed set-point flow rate. The visible signal may cause one or more light-emitting diodes (LEDs) to illuminate to provide a visible alarm to the user. A start up/abort printed circuit board (not shown) controls the run and abort inputs of the timer 402 (see FIG. 4).

The start signal is an input to the controller 202 from the touchpad 214 or the timer 402 (associated with one of the ports 308), which will initiate a sampling cycle in the controller 202 hardware. When the individual ports 308a, 308b, 308c, . . . , 308n on the controller 202 receive the start signal, the controller 202 will start a sampling cycle by controlling isolator controller 504. The controller 202 then informs the touchpad 214 that a sampling cycle instruction signal has been issued.

The abort signal is an input to the controller 202 that halts the sampling cycle already in progress. When the individual ports 308a, 308b, 308c, . . . , 308n of the controller 202 receive the abort signal, the controller 202 will instruct the touchpad 214 by controlling isolator controller 504. The controller 202 then informs the touchpad 214 that the sampling cycle instruction signal has been halted.

When a sampling cycle is in progress, the individual ports 308a, 308b, 308c, . . . , 308n of the controller 202 will instruct the touchpad 214 and, if necessary, the SCADA interface 410 (in order to communicate with a separate facility system), that a sampling cycle is in progress and this signal will remain active for the remainder of the sampling duration.

When an individual port 308a, 308b, 308c, . . . , 308n is in the middle of a sampling cycle and an air flow deficiency is detected, the controller 202 will broadcast a 1 cfm error to the port that is sampling. The power input to the SCADA system will go from active to non-active during a sampling cycle for that port, and continue on/off for the duration of the sampling cycle or until the 1 cfm error is removed.

The touchpad 214 includes a display 702. The display 702 includes switches for powering up the touchpad 214 and the individual ports 308a, 308b, 308c, . . . , 308n on the controller 202 to which the touchpad 214 is connected One or more LEDs provides a visual confirmation that the power on the touchpad 214 has been activated and that the vacuum pump 208 is on. The display 702 is adapted to display accurate flow rate information regardless of the composition of the air (i.e., amount of nitrogen, argon, and carbon dioxide gases).

Each touchpad 214 includes its own power source 704, or it may be electrically connected and powered by the controller 202 through cable 706 (which is the same as cable 218 in FIG. 2), which provides voltage to the touchpad 214. The touchpad 214 utilizes a shielded plenum wire consisting of less than about 2 watts of power.

The touchpad 214 may include a cable 708 that provides a signal to one of the individual ports 308a, 308b, 308c, ..., 308n on the controller 202, or this may be a wireless connection. The touchpad 214 may include a second cable 710 that provides a signal to one of the other individual ports 308a, 308b, 308c, ..., 308n on the controller 202, or this may also be a wireless connection. The number of cables tying the touchpad 214 to the individual ports 308a, 308b, 308c, ..., 308n on the controller 202 will depend on the number of ports the touchpad 214 is controlling.

Figure 8:
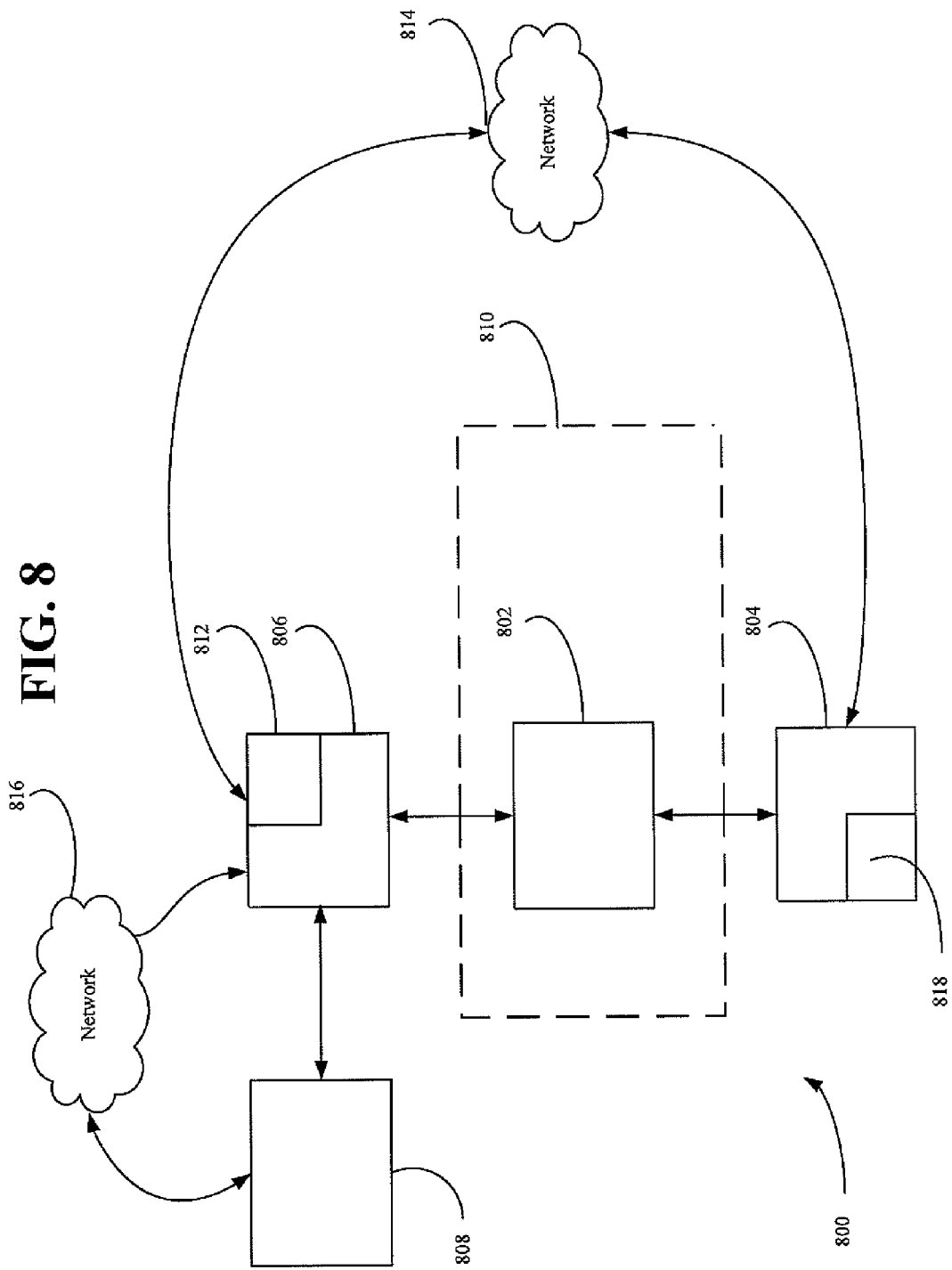
FIG. 8 is a block diagram of an air sampling/monitoring system according to another embodiment of the present invention for use in the clean room of FIG. 1.

Turning now to FIG. 8, shown therein is a block diagram of an air sampling/monitoring system 800 according to another embodiment of the present invention for use in the clean room 102. The air sampling/monitoring system 800 includes an air sampling device 802, a controller 804, a base module 806, and a control panel 808.

The air sampling device 802 in FIG. 8 is shown located within a laminar air flow hood or isolation chamber 810, which may include a high efficiency particulate air (HEPA) filter (not shown). The the air sampling device 802 and the controller 804 are provided in a single portable device that may be placed in any location within the clean room 102, or outside the clean room 102, as necessary.

The controller 804 may include a self-contained air sampling pump 818. The air sampling device 802 is attached to the controller 804 as shown using a vacuum air tube that is about seven feet or less. The features of the controller 804 are similar to those described above in connection with the description of FIG. 3. For example, the controller 804 provides for a 1 cfm air flow error detection during an air sampling cycle, and it is easily connected to a facilities' SCADA.

The base module 806 is electrically connected to the controller 804 and air sampling device 802, or wirelessly connected to the controller 804 via network 814 using receiver/transmitter 812. The base module 806, which is typically fixed at a location near the air sampling device 802, routes signals between the controller 804 and the control panel 808 either by wire or wireless network 816 using receiver/transmitter 812. Thus, the panel 808, which may be wall-mountable, provides the user with input/output control of the air sampling device 802 by way of the controller 804. Because the configuration in FIG. 8 is wireless, the air sampling/monitoring system 800 does not require any penetration of walls, ceilings, or floors for routing of cables or air tubes. Thus, the installation costs are much less than other embodiments described previously.

Figure 9:
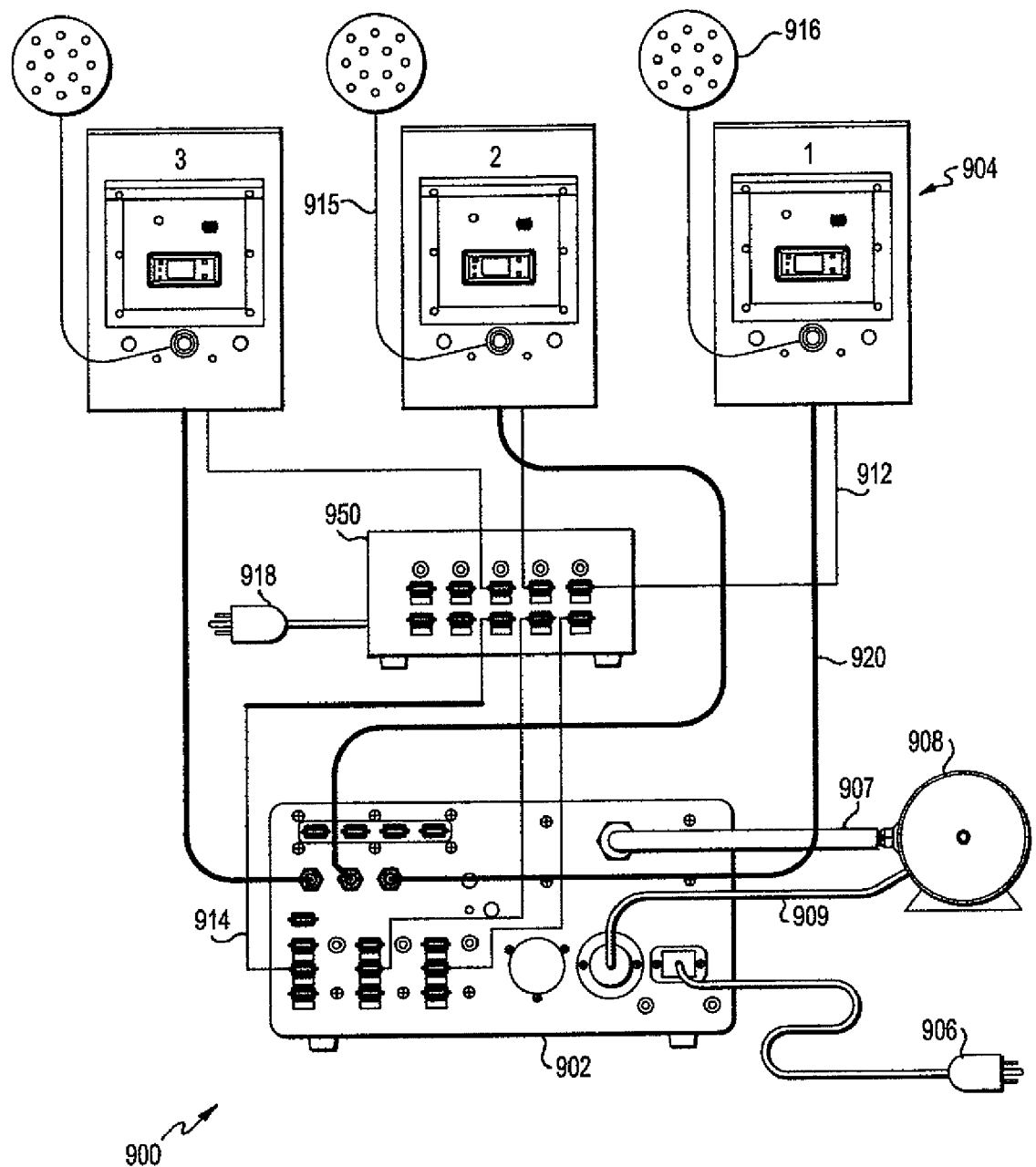
FIG. 9 is a block diagram of an air sampling/monitoring system according to another embodiment of the present invention, having an inline flow switch.

Referring to FIG. 9, an air sampling/monitoring system 900 is shown in accordance with an alternative embodiment of the present invention. The system 900 includes a controller 902, inline flow switch modules 904, and a flow switch controller 950. The controller 902 includes the operations of the controller 204 of FIGS. 1-8. In addition, the controller 902 communicates with the flow switch controller 950 and the inline flow switch modules 904 to control operation of the inline flow switch module 904, which generates a flow alarm in the event the flow recognized at the flow switch module 904 is outside of a desired flow rate.

As shown, a separate flow switch module 904 is associated with each air sampling device 916. Each flow switch 904 is connected to the controller 902 by a vacuum air line 920. A vacuum pump 908 is also connected to the controller 902 by hose 907. The controller 902 separates the air flow created by the vacuum pump 908 amongst the various vacuum air lines 920 leading out from the controller 902 to the flow switches 904. The vacuum 908 is in flow communication with a manifold that steers the vacuum to the proper solenoid to direct the air flow to the desired one or more of the air lines 920. The controller 902 is configured so that each vacuum air line 920 has 1 cfm of air, which is the desired air flow rate needed to conduct a proper sampling at the air sampling device 916. In the embodiment of FIG. 2, the various air sampling devices 216 were in direct flow communication with the controller 202 via the air tubes 220. In the present embodiment of FIG. 9, however, the inline flow switches 904 are positioned between the air sampling devices 916 and the controller 202.

In addition, the flow switch modules 904 are in electrical communication with the flow switch controller 950 via the flow control line 912. The flow switch controller 950 is in electrical communication with the main controller 902 via the control lines 914. A separate control line 914 is provided for each flow switch 904 and respective air sampling device 916. As shown, the vacuum air line 920 and control lines 914 are connected at a respective port of the controller 902, such as the ports 308 shown for controller 202 in FIG. 3. The ports are dedicated to the respective flow switch modules 904 and not shared with any other sampling ports. Though the controllers 902, 950 and flow switch module 904 are shown in wired communication with one another, it should be appreciated that those devices can be in wireless communication. Accordingly, the controller 902 activate the various ports to activate a respective flow switch module 904.

The various flow switch modules 904 are shown connected in a parallel manner to the main controller 902 and to the flow switch controller 950. It should be apparent, however, that the controllers 902, 950 and flow switch 904 can be connected in any suitable manner. For instance, the flow switches 904 can be directly connected to the main controller 902, so that a flow switch controller 950 need not be utilized. Or, the flow switches 904 can have identification codes, and the controller 902 can communicate with the flow switches 904 by use of those ID codes. The vacuum has a power cord 909 which plugs into the controller 902 for its power supply. The controller 902 has an AC plug 906 which supplies power to the system 900. The flow switch controller 950 also has an AC cord 918 which supplies power to the flow switch controller 950.

The flow switches 904 monitor the actual flow rate that is realized by the respective air sampling device 916. If the flow rate on the vacuum air line 920 is off by ±5% (i.e., not within the range of 0.95-1.05 cfm), then the flow switch 904 generates an alarm signal. However, the sampling cycle continues until the user decides to abort the sampling cycle. Preferably, the flow switch 904 includes an 8 second delay before the alarm signal is generated. That delay accounts for fluctuations that may occur during initial start-up of the system 900. A typical sampling cycle may last between 10 minutes and 3 hours.

Figure 10:
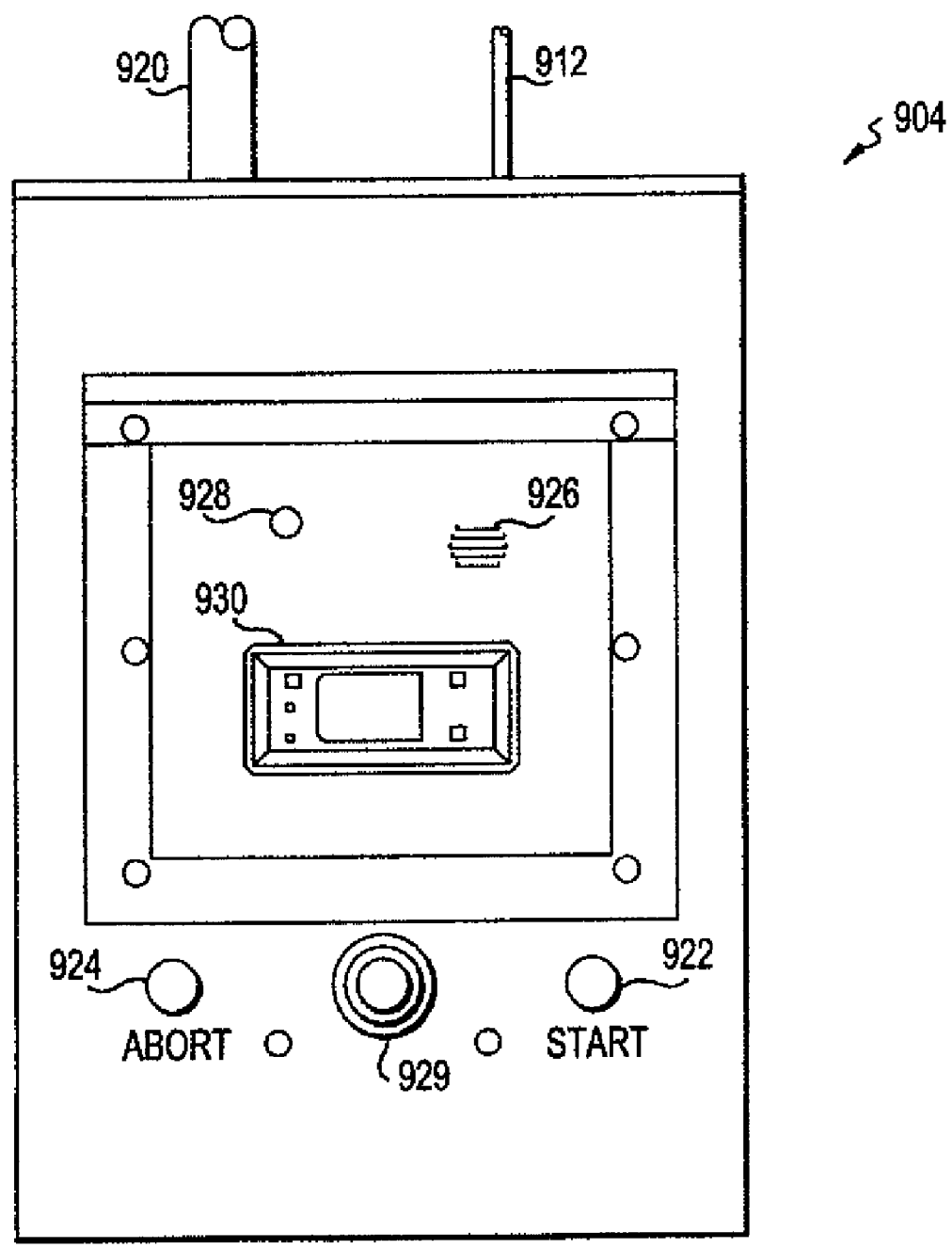
FIG. 10 is a detailed front view of the inline flow switch.

The flow switch controller 950 also sends a flow switch disconnect signal to the main controller 902 over the control line 914 in response to the user manually activating and abort button 924 (FIG. 10). In response to the disconnect signal, the controller 902 cuts off the flow of air to the respective flow switch 904. In addition, it should be appreciated that the flow switch 904 can optionally transmit the alarm signal to the flow switch controller 950, which can then send an alarm signal back to the other flow switch modules 904 to generate an alert.

Turning to FIG. 10, the flow switch module 904 is shown in greater detail, and having the vacuum air line 920 and the flow control line 912. The flow switch 904 has a start button 922, stop button 924, and dual alert alarm indicators 926, 928. The start button 922 is used to manually activate a sample period. In response to the start button 922 being activated, the flow switch 904 sends a signal to the main controller 902 via the flow controller 950. The main controller 902 activates the vacuum 904 to cause the air flow on the vacuum air line 920 to the respective air sampling device 916 via the atrium air flow line 915.

The stop button 924 aborts the sampling cycle and turns off the vacuum air flow for the air sampling device 916. When the stop button 924 is activated, a stop signal is sent to the main controller 902 via the flow controller 950. In response, the main controller 902 turns off the vacuum 904 to the respective flow switch module 904. The user (technician) may abort the sampling cycle for various reasons, including that the alarm has been signaled by the flow switch module 904. The alarm indicators 926, 928 indicate if the air flow at the flow switch 904 is out of specification. An audible alarm is also provided to further alert the user when the flow rate is faulty. The alarm continues until the abort switch 924 is activated, or the error conditions are removed and the flow rate returns to the desired 1 cfm.

Thus, in accordance with the preferred embodiment, the air flow is only activated and de-activated when the user manually operates the buttons 922, 924. And, the start/stop buttons 922, 924 only activate and de-activate the air flow for the particular flow switch module 904 at which the user manually operated those buttons 922, 924. That way, the user can verify that the air sampling device 916 is properly set up and ready to conduct a sampling cycle. However, it should be appreciated that the system can be configured so that the user can start and stop air flow to other or all of the flow switch modules 904 in the system, either simultaneously or at other times, at any of the flow switch modules 904, or at either of the controllers 902, 950.

Figure 11:
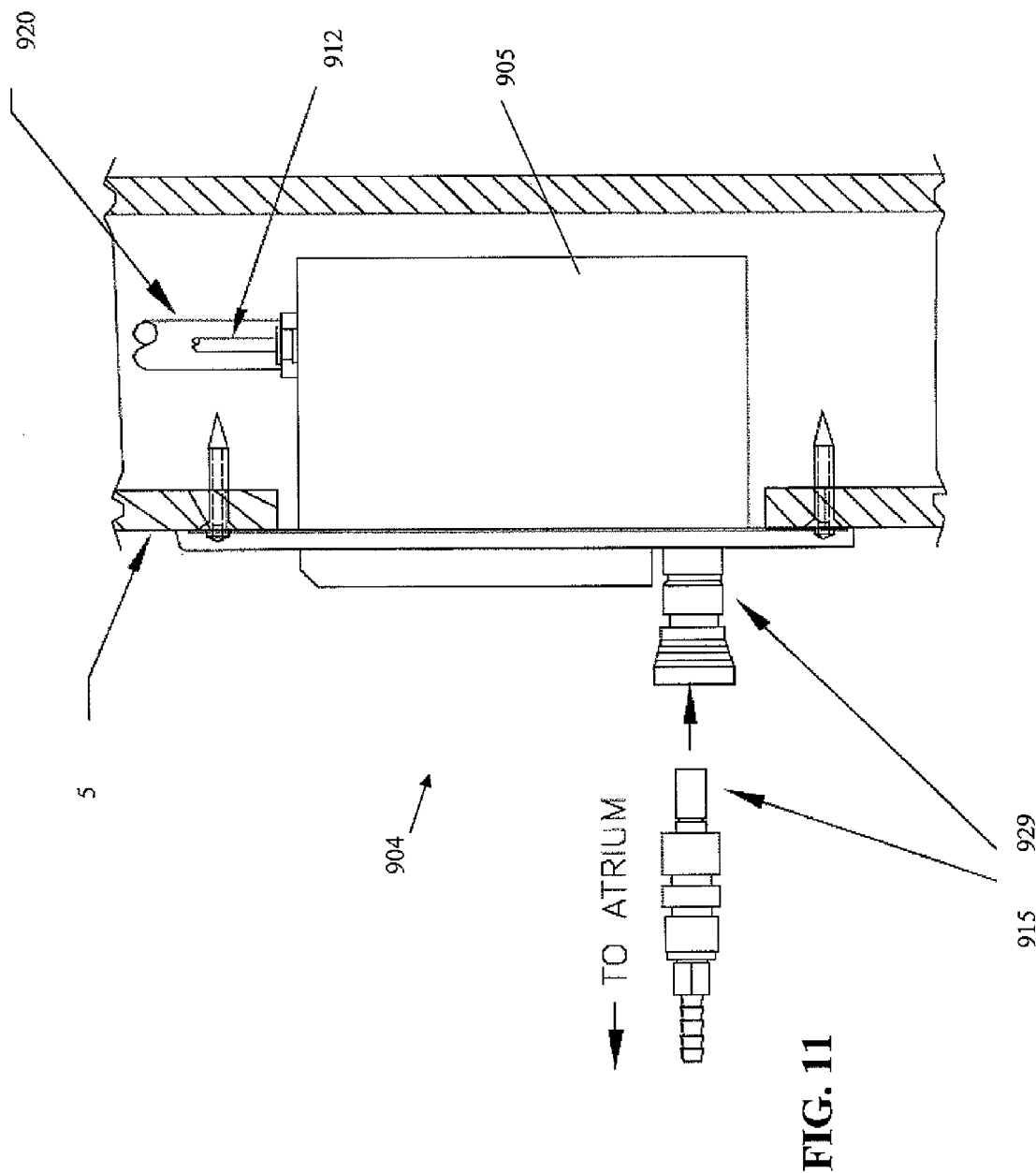
FIG. 11 is a side view of the inline flow switch.

An air flow plug adapter 929 is provided on the front face of the flow switch 904. The plug adapter 929 is shown in FIG. 11 connecting to the atrium air flow line 915. The plug 929 is preferably a quick disconnect, so that the atrium line 915 can be quickly connected and disconnected and replaced, if necessary. As further shown, the flow switch 904 can be contained within a housing 905 and mounted either internal to a wall 5, as shown, or externally to the face of the wall 5.

Figure 12:
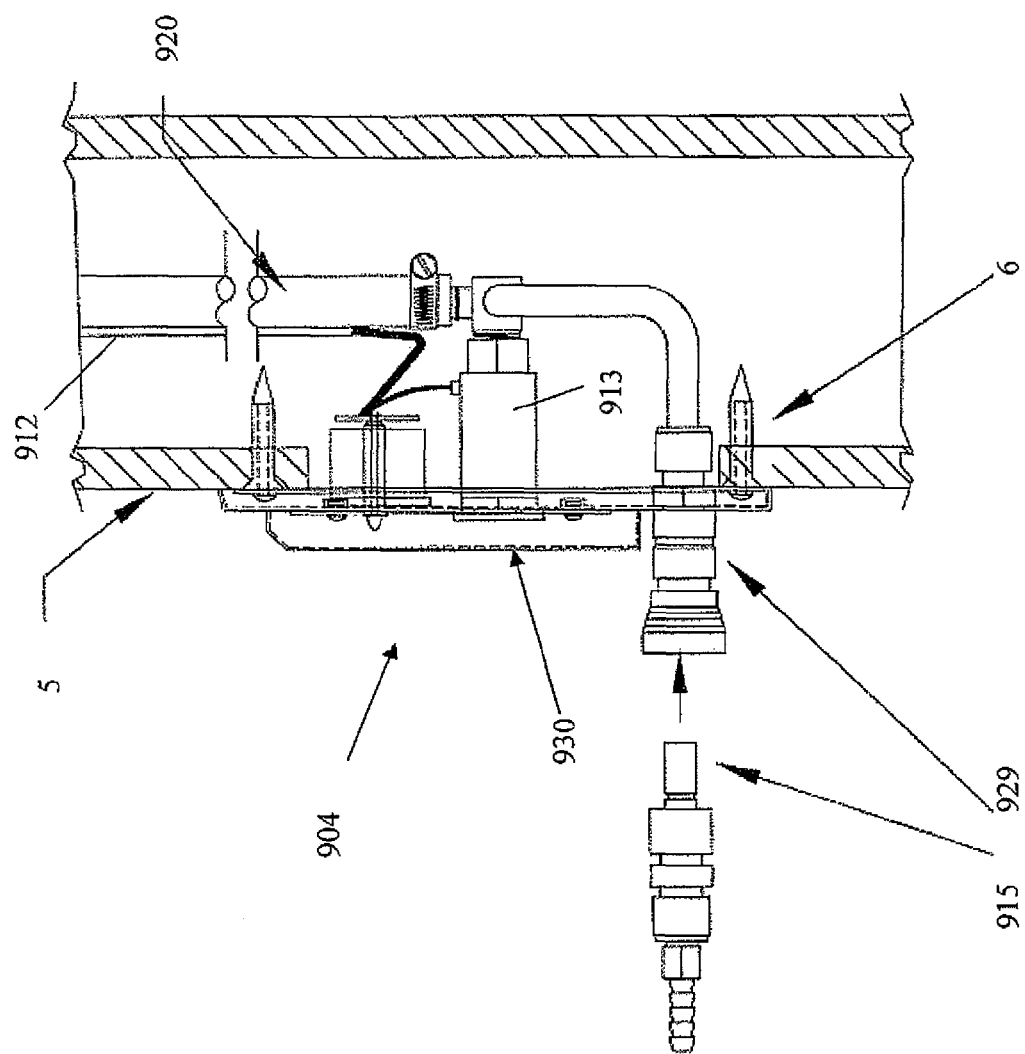
FIG. 12 is another side view of the inline flow switch with the housing removed.
Figure 13A:
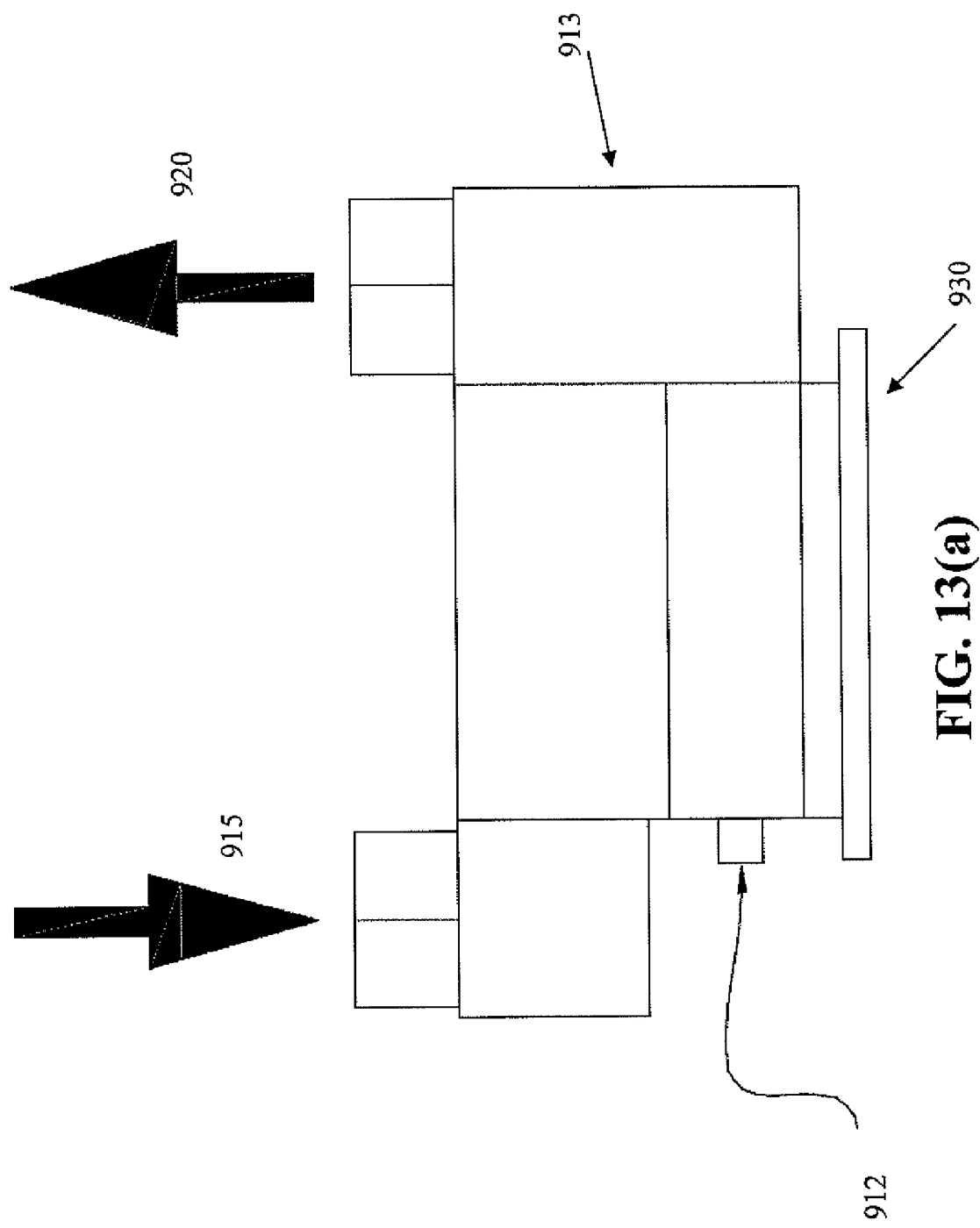
FIG. 13(*a*) is a top view of the flow detector used in the flow switch module.

Referring to FIG. 12, the flow switch 904 is shown with the housing 905 removed to show the internal workings. The vacuum line 920 connects through to the plug 929, for easy connection to the atrium line 915. As further shown in FIG. 13(a), one end of the flow detector 913 is connected to the flow line 920, and an opposite end is connected to the atrium air flow line 915, which leads to the air sampling device 916. The flow detector 913 detects the flow rate coming in from line 915 and passing through to line 920. The detector 913 generates an alarm signal if the detected air flow rate is not within the parameters set by the user. If an alarm is generated, the alarm indicators 926, 928 are activated. Thus, the signal line 912 is connected to a data port on the detector 913 (FIGS. 12 and 13(a)) and to the indicators 926, 928. In addition, the detection performed by the flow detector 913 is independent of the flow rate detection performed at the main controller 902, so that the flow rate is simultaneously monitored at two locations during a sampling cycle.

Optionally, a signal can also be sent back along alarm line 912 to the air flow controller 950. The air flow controller 950 can send the alarm condition to the other flow switches 904 to activate their respective indicators 926, 928 and audible alarm.

The flow detector 913 is positioned near the air sampling device 916, whereas the main controller 902 is remotely located outside the clean room. In accordance with the preferred embodiment, the atrium air flow hose 915 is from about 1-20 feet in length, so that the flow switch module 904 is located in the clean room with the air sampling device 916. Thus, any break in that line 915 may cause a sound which can be detected by the user. Because the flow detector 913 is relatively close to the actual sampling devices 916, it ensures that the flow rate at the air sampling devices 916 is accurate. Thus, for instance, the flow detector 913 will prevent against error in the flow rate due to a break in the line 920 between the controller 902 and the flow switch 904. An improper flow rate can also occur where the flow line is kinked, if the hoses are not properly connected, or if the vacuum motor 908 is not turned on or working properly. Often, the vacuum line 920 is within a wall or near noisy equipment, so that a break is difficult to detect.

Figure 13B:
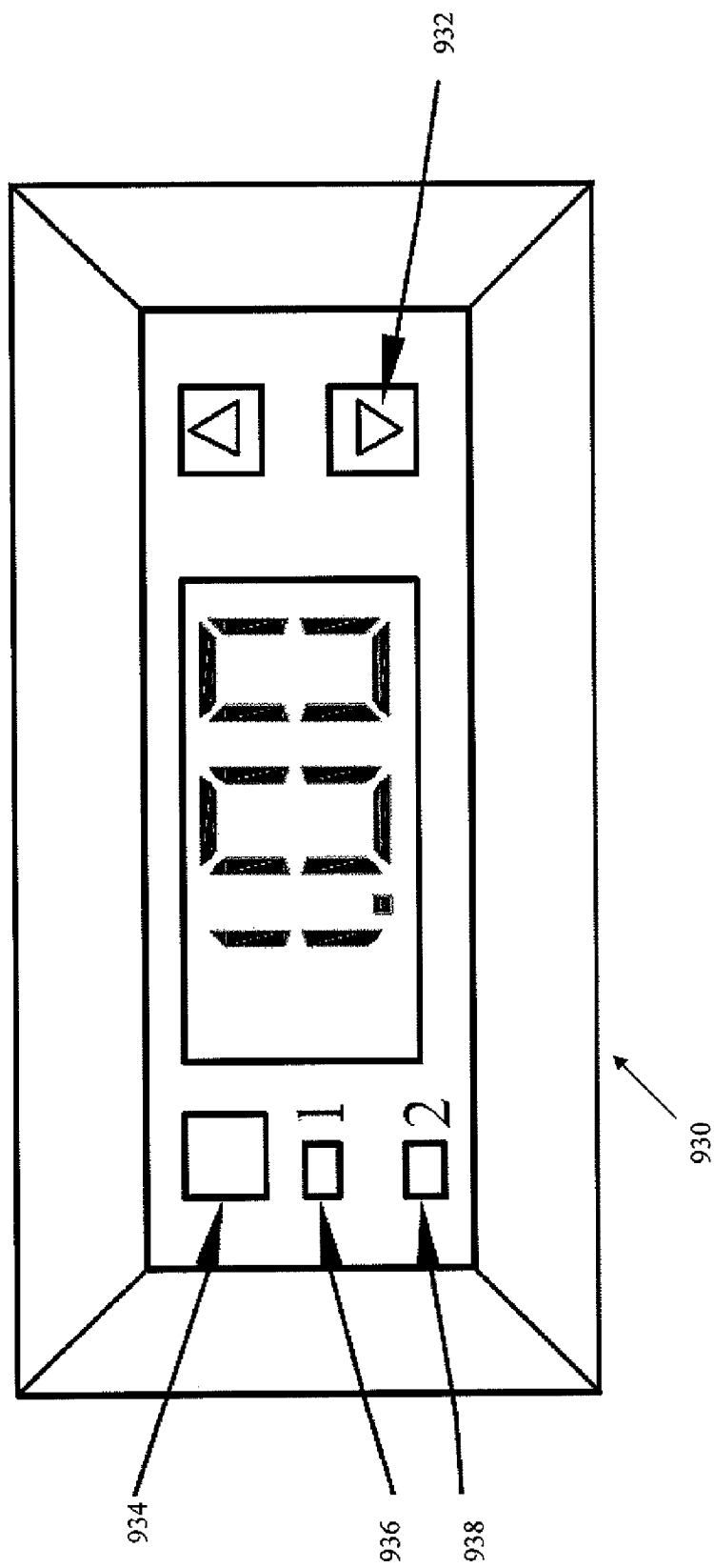

Turning to FIG. 13(b), the control panel and display 930 of the flow switch device 904 is shown in further detail. The control panel 930 has various buttons that allow the user to set the desired range of flow rates. If the detected flow rate is outside of that range, the alarm signal is generated. The desired rate of 1.00 cfm is shown in the display 930. That rate can be changed by pressing the up/down arrows 932 to increase or decrease the value that is displayed. Optionally, the desired rate selected by the user can then be transmitted to the main controller 902 so that the proper flow rate can be provided on the vacuum air line 920.

The display panel 930 also has a programming button 934 to further assist the user (technician on site, or manufacturer) to set the desired flow rate and other display options, such as whether to display values in cubic feet per minute, or cubic liters per minute Light indicators 936, 938 are provided as an easy reference for the user to confirm that the flow switch 904 is operating properly and that the flow rate is being detected. For instance, one light 936 can indicate that the flow rate is above the minimum desired value (i.e., 0.95 cfm), and the other light 938 can display that the flow rate is below the maximum desired value (i.e., 1.05 cfm). During a sampling cycle, the air flow rate detected by the detector 913 is displayed so that the user can observe that the correct air flow is within specification and confirm that air is flowing at the site being tested.

In addition, the user (technician) can observe that the respective port of the controller 902 is activated and that the flow switch module 904 is plugged into the controller 950, which results in the display panel 930 being activated. Under normal conditions, the flow rate detected by the main controller 902 should be the same as that detected by the flow switch 904 and displayed on the display 930.

Figure 14:
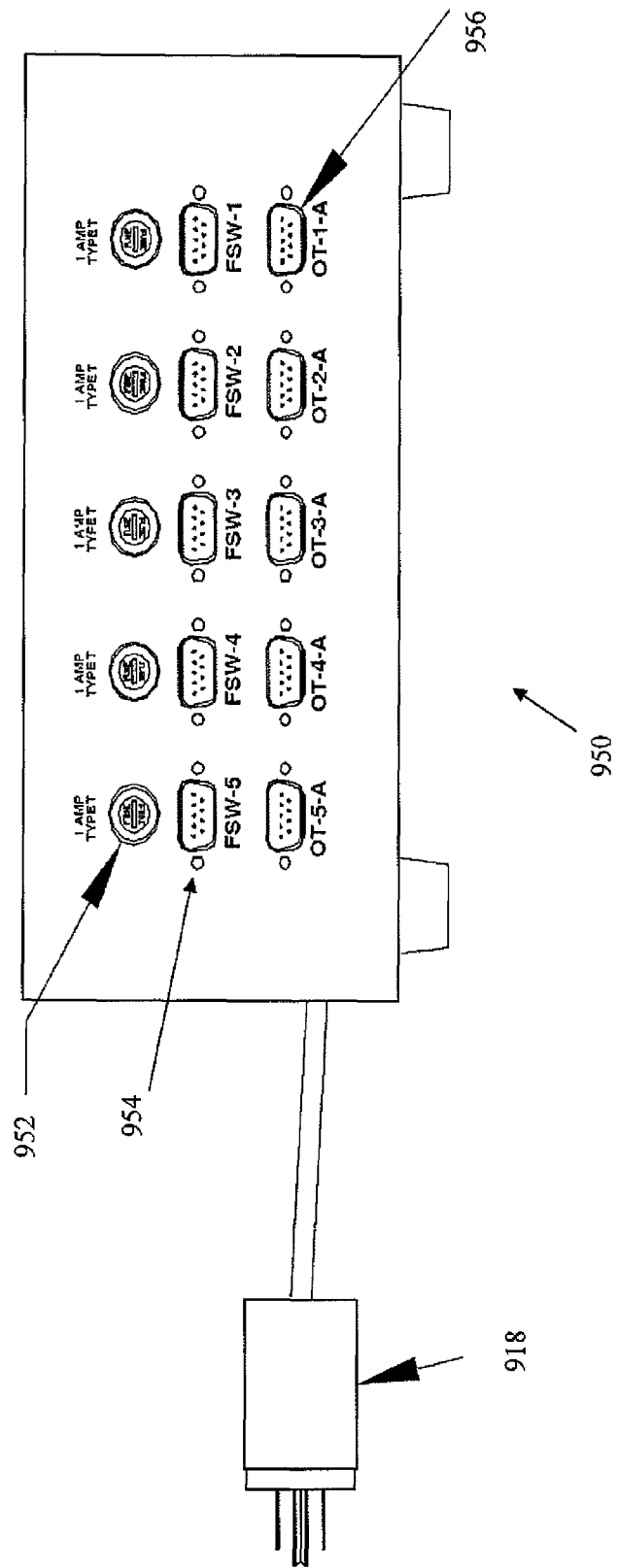
FIG. 14 is a rear view of the controller used with the inline flow switch.

As shown in FIG. 14, the air flow controller 950 has a row of amps 952, a row of inputs 954, and a row of outputs 956. The rows are aligned so that each column contains a single amp 952, input 954 and output 956, which is associated with a respective flow switch module 904. The inputs 954 receive the flow control line 912 from the flow switch 904, and the outputs 956 connect to the control line 914 leading to the main controller 902. The input 954 also provide power to the flow switch module 904 to power the flow switch 904. The flow controller 950 is preferably located outside of the clean room in an adjacent room or with the main controller 902. The system is modular, so any number of flow switch devices 904 can be plugged into the flow switch controller 950 as needed for a particular application.

The flow switch controller 950 isolates the flow switches 904 from the main controller 902. Thus, the DC voltage and logic signals connected to the inline flow switch 904 are isolated from the main controller 902. This is done so that a short in the controller 902 does not cause a short in the flow switch 904, which can then be controlled by another device. The flow switch module 904 is modular and electrically isolated from the main controller's 902 DC voltage and DC ground system. Accordingly, the flow switch controller 950 is essentially a repeater that passes signals between the flow switches 904 and the main controller 902, generates the DC voltage needed by the flow switches 904, and electrically isolates the main controller 902.

Figure 15:
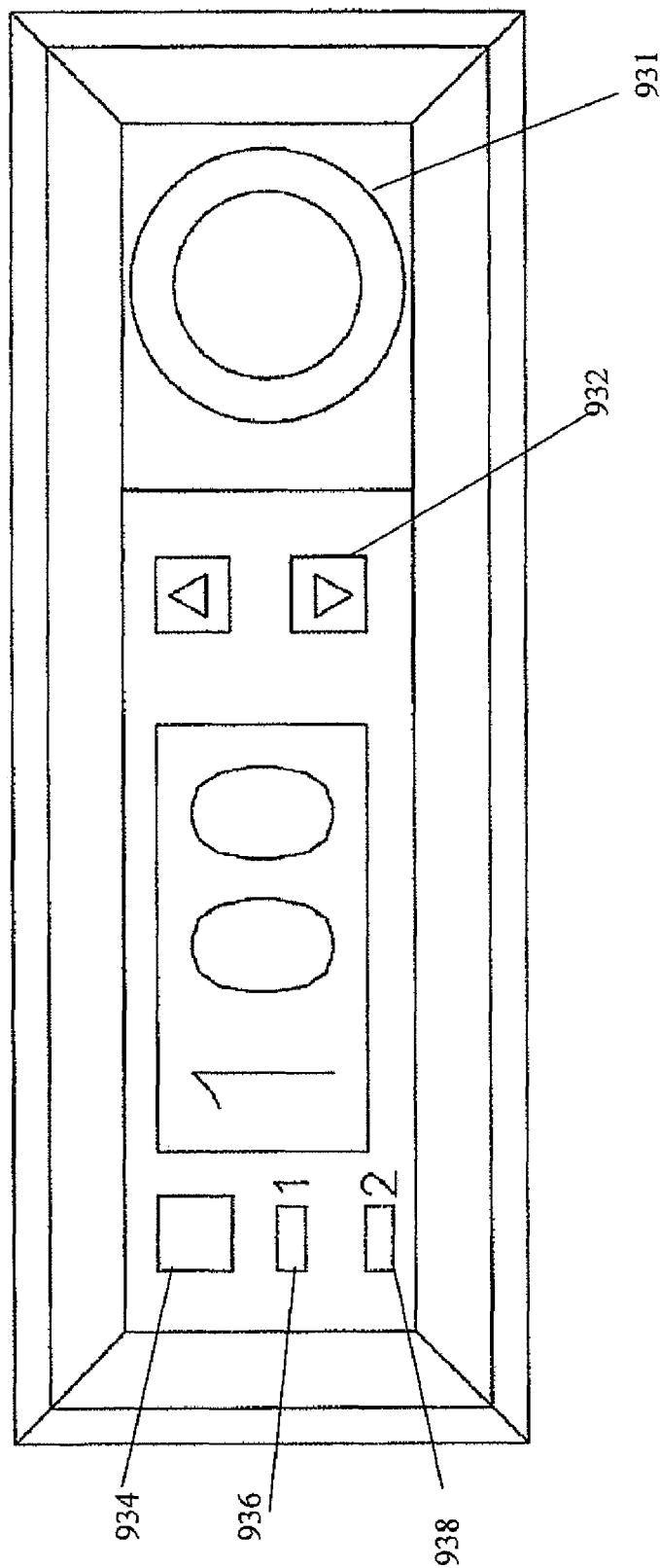
FIG. 15 is a front view of the control panel of the main controller.

Turning to FIG. 15, the control panel of the main controller 902 is shown. The control panel of controller 902 is used to operate the flow rate detection at the main controller 902. It has similar control buttons as the control panel of the flow switch 904, which is shown in FIG. 13(b). However, the control panel of the main controller 902 also has a flow control knob (or pinch valve). The control knob 931 allows the user to adjust the air flow on the lines 920. The air flow may need to be adjusted depending on several factors, such as the length of the hose 920 and the number of flow switches 904 that are activated at any one time.

It should be apparent that the flow switch module 904, flow switch controller 950 and main controller 902 can each be implemented by a processor or other computing platform to control operation of those devices. In addition, although the main controller 902 and the flow switch controller 950 are shown and described as being separate devices, they can be integrated into a single unit. In addition, the main controller 902 and the flow switch controller 950 can each have separate processors, or be a single processor.

The system 900 can be a network configuration or a variety of data communication network environments using software, hardware or a combination of hardware and software to provide the processing functions. All or parts of the system and processes can be stored on or read from computer-readable media, such as a CD-ROM or instructions received online and carried over a transmission line or contained in a customized hardwired application specific integrated circuit (ASIC).

In addition, the system shown in FIG. 9 can be used with a touchpad, such as the touchpad 214 shown in FIG. 2, which can be connected by wire or wirelessly. In that instance, the flow switch module 904 would be positioned between each air sampling device 216 and the controller 202, along air tube 220. The touchpad 214, and its operations, can be a separate device, or integrated into one or more of the flow switches 904.

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

I claim:

1. A method for collecting a volume of air from a controlled environment within a facility, comprising the steps of:
providing at least one air sampling device within the controlled environment;
providing at least one flow switch module within the controlled environment and in flow communication with one of the at least one air sampling device, the at least one flow switch module having a flow rate detector disposed therein and configured to detect an air flow rate through the flow switch module;
providing a vacuum source;
providing a first controller outside the controlled environment and in flow communication with the at least one flow switch module, the first controller further in electrical communication with the vacuum source to control the vacuum source to draw a predetermined volume of air through the at least one air sampling device via the at least one flow switch module at an actual flow rate; and,
detecting at the at least one flow switch module, when the actual flow rate through the at least one flow switch module falls below or above a predetermined value.

2. The method of claim 1, further comprising detecting at the first controller when the actual flow rate through the first controller falls below or above the predetermined value.

3. The method of claim 1, further comprising providing a second controller outside the controlled environment and in electrical communication with the at least one flow switch module and the first controller.

4. The method of claim 3, further comprising outputting from the at least one flow switch module an alarm signal from the at least one flow switch module in response to said detecting.

5. The method of claim 4, further comprising communicating the alarm signal from the at least one flow switch module to the second controller, and from the second controller to the first controller to stop the vacuum source.

6. The method of claim 5, wherein the second controller further activates an alarm at each of the at least one flow switch modules.

7. The method of claim 3, further comprising communicating a control signal from the at least one flow switch module to the second controller, and from the second controller to the first controller to activate the vacuum source.

8. The method of claim 3, further comprising communicating a control signal from the at least one flow switch module to the second controller, and from the second controller to the first controller to stop the vacuum source.

9. The method of claim 1, further comprising communicating a control signal from the at least one flow switch module to the first controller to activate the vacuum source.

10. The method of claim 1, further comprising communicating a control signal from the at least one flow switch module to the first controller to stop the vacuum source.

11. The method of claim 1, wherein the at least one air sampling device comprises an atrium.

12. The method of claim 1, wherein the predetermined value is 1 cfm.

13. The method of claim 1, wherein the predetermined value is 0.95-1.05 cfm.

14. The method of claim 1, further comprising generating an alarm at the flow switch module in response to detecting that the actual flow rate falls below or above the predetermined value.

15. The method of claim 14, wherein generating the alarm comprises activating a light at the flow switch module.

16. A sampling system for collecting a volume of air in a controlled environment within a facility, comprising:
at least one air sampling device within the controlled environment;
at least one flow switch module within the controlled environment and in flow communication with one of the at least one air sampling device, the at least one flow switch module having a flow rate detector disposed therein and configured to detect an air flow rate through the flow switch module;
a vacuum source; and,
a first controller outside the controlled environment and in flow communication with the at least one flow switch module, the first controller further in electrical communication with the vacuum source to control the vacuum source to draw a predetermined volume of air through the at least one air sampling device via the at least one flow switch module at an actual flow rate;

wherein the at least one flow switch module detects when the actual flow rate through the at least one flow switch module falls below or above a predetermined value.

17. The sampling system of claim 16, wherein the first controller detects when the actual flow rate through the first controller falls below or above the predetermined value.

18. The sampling system of claim 16, further comprising a second controller outside the controlled environment and in electrical communication with the at least one flow switch module and the first controller.

19. The sampling system of claim 18, wherein the at least one flow switch module outputs an alarm signal in response to detecting that the actual flow rate through the at least one flow switch module falls below or above the predetermined value.

20. The sampling system of claim 19, wherein the at least one flow switch module communicates the alarm signal to the second controller, and the second controller communicates the alarm signal to the first controller to stop the vacuum source.

21. The sampling system of claim 20, wherein the second controller further activates an alarm at each of the at least one flow switch modules.

22. The sampling system of claim 18, wherein the at least one flow switch module communicates a control signal to the second controller, and the second controller communicates the control signal to the first controller to activate the vacuum source.

23. The sampling system of claim 18, wherein the at least one flow switch module communicates a control signal to the second controller, and the second controller communicates the control signal to the first controller to stop the vacuum source.

24. The sampling system of claim 16, wherein the at least one flow switch module communicates a control signal to the first controller to activate the vacuum source.

25. The sampling system of claim 16, wherein the at least one flow switch module communicates a control signal to the first controller to stop the vacuum source.

26. The sampling system of claim 16, wherein the at least one air sampling device comprises an atrium.

27. The sampling system of claim 16, wherein the predetermined value is 1 cfm.

28. The sampling system of claim 16, further comprising a first vacuum tube connected between the at least one air sampling device and the at least one flow switch module, and a second vacuum tube connected between the first controller and the at least one flow switch module.

29. The sampling system of claim 16, further comprising a plurality of flow switch modules.

30. The sampling system of claim 16, wherein the predetermined value is 0.95-1.05 cfm.

31. The sampling system of claim 16, further comprising a light indicator at the flow switch module, the light indicator activating in response to the flow switch module detecting that the actual flow rate falls below or above the predetermined value.

32. The method of claim 1, wherein the at least one flow switch module further comprises a display panel.

33. The method of claim 1, wherein the at least one flow switch module further comprises a visual alarm indicator.

34. The method of claim 1, wherein the at least one flow switch module further comprises an audible alarm indicator.

35. The method of claim 1, wherein the at least one flow switch module further comprises a means for manually inputting a desired flow rate.

36. The method of claim 1, wherein the at least one flow switch module further comprises means for manually stopping and starting the flow of air therethrough.

37. The sampling system of claim 16, wherein the at least one flow switch module further comprises a display panel.

38. The sampling system of claim 16, wherein the at least one flow switch module further comprises a visual alarm indicator.

39. The sampling system of claim 16, wherein the at least one flow switch module further comprises an audible alarm indicator.

40. The sampling system of claim 16, wherein the at least one flow switch module further comprises a means for manually inputting a desired flow rate.

41. The sampling system of claim 16, wherein the at least one flow switch module further comprises means for manually starting and stopping the flow of air therethrough.

* * * * *